(12) United States Patent
Schellenberger et al.

(10) Patent No.: US 6,365,410 B1
(45) Date of Patent: Apr. 2, 2002

(54) DIRECTED EVOLUTION OF MICROORGANISMS

(75) Inventors: Volker Schellenberger, Palo Alto; Amy D. Liu, Mountain View; Olga V. Selifonova, Los Altos, all of CA (US)

(73) Assignee: Genencor International, Inc., Palo Alto, CA (US)

(*) Notice: Subject to any disclaimer, the term of this patent is extended or adjusted under 35 U.S.C. 154(b) by 0 days.

(21) Appl. No.: 09/314,847

(22) Filed: May 19, 1999

(51) Int. Cl.$^7$ ............................................. C12N 15/74

(52) U.S. Cl. ................. 435/488; 435/440; 435/252.3; 435/252.33; 435/243; 435/320.1

(58) Field of Search ............................... 435/440, 467, 435/471, 476, 252.3, 252.33, 320.1, 243, 488

(56) References Cited

U.S. PATENT DOCUMENTS

| | | | |
|---|---|---|---|
| 5,716,785 A | 2/1998 | Van Gelder et al. | ............ 435/6 |
| 5,807,522 A | 9/1998 | Brown et al. | ................. 422/50 |

FOREIGN PATENT DOCUMENTS

| | | |
|---|---|---|
| EP | 0 666 316 A2 | 9/1995 |
| WO | WO/95/35505 | 12/1995 |
| WO | WO 98/21340 | 5/1998 |

OTHER PUBLICATIONS

Holly S. Murphy et al. *Escherichia coli* cells exprissing a mutant gly(glycine tRNA) Gene hav a UVM–Constitutive-Phenotype: Implications for mechanisms underlyint the mutA or mutC Mutator Effect Journal of Bacterology, Dec. 1997, pp. 7507–7514 vol. 179, No. 23.*
Edward C Cox et al. Structure and coding properties of a dominant *Escherichia coli* mutator gene, mutD Apr. 1983 vol. 80 pp. 2295–2299.*
Kyoko Takano et al. Structure asnd function iof dnaQ and mutD mutators of *Escherichia coli* (1986) pp. 9–13.*
Sharon A. Taft–Benz and Roel M. Schaaper Mutationkl analysis of the 3'–5' proofreading exonuclease of *Escherichia coli* DNA polymerase III Sep. 1997 vol. 26 No. 17 4005–4011.*
Masao Maruyama et al. A Dominant (mut D5) and a Recessive (dnaQ49) Mutator of *Escherichia coli*(1983) 167, 757–771.*
Marc Prudhomme et al Mismatch Repair Genes of *Streptococcus pneumoniae*:hexA confers a Mutator Phenotype in *Escherichia coli* by Negative Complementation Journal of IBacterology Nov. 1991 pp. 7196–7203 vol. 173, No. 22.*
Francesca Ginette et al. *Bacillus subtilis* muts mutl operon: identification, nucleotide sequence and mutagenesis (1996), pp. 142 2021–2029.*

Copy of International Search Report for PCT/US00/13337.
Roa, et al., "Changing the substrate specificity of penicillin G acylase from *Kluyvera citrophila* through selective pressure," Biochem. J. (1994) 303, pp. 869–876 (XP–000972422).
Naki, et al., "Selection of a subtilisin–hyperproducing Bacillus in a highly structured environment," Appl. Microbiol. Biotechnol. (1998) 49: pp. 290–294 (XP–000972404).
Schellenberger, "Directed evolution of subtilisin for improved surface proteolysis," (1998) BTEC 73, vol. 216, No. 1–3 (XP000972454).
Yamagishi, et al., "Mutational analysis of structure—activity relationships in human tumor necrosis factor–alpha," Protein Engineering, vol. 3, No. 8, pp. 713–719 (1990) (XP–000971051).
DiFrancesco, et al., "The Interaction of DNA Polymerase III and the Product of the *Escherichia coli* Mutator Gene, mutD," Journal of Biological Chemistry (1984) vol. 259, No. 9, Issue of May 10, pp. 5567–5573 (EX–000974352).
Greener, et al., "An Efficient Random Mutagenesis Technique Using an *E. coli* Mutator Strain," Molecular Biotechnology (1997) vol. 7, pp. 189–195 (XP–000974365).
Alexandre et al., "Relationship between ethanol tolerance, lipid composition and plasma membrane fludity in *Saccharomyces cerevisiae* and *Kloeckera apiculata*," FEMS Microbiol, Lett, vol. 124 (1), pp. 17–22 (1994).
Aono et al., "Preparation of Organic Solvent–tolerant Mutants from *Escherichia coli* K–12," Agric. Biol. Chem., vol. 55(7), pp. 1935–1938 (1991).
Bennett et al., "Rapid evolution in response to high–temperature selection," Nature, vol. 346, pp. 79–81 (1990).
Coia et al., "Use of Mutator Cells as a Means for Increasing Production Levels of a Recombinant Antibody Directed Against Hepatitis B," Gene, vol. 201, pp. 203–209 (1997).
Cox et al., "Structure and coding properties of a dominant *Escherichia coli* mutator gene, mutD," Proc Natl. Acad Sci USA, vol. 80, pp. 2295–2299 (1983).
Cruden et al., "Physiological Properties of a Pseudomonas Strain Which Grows with p–Xylene in a Two–Phase (Organic–Aqueous) Medium," Appl. Environ. Microbiol, vol. 58(9): pp. 2723–2729 (1992).
de Bont, "Solvent–tolerant bacteria in biocatalysis," Trends in Biotechnology, vol. 16: pp. 493–499 (1998).
de Visser et al, "Diminishing Returns from Mutation Supply Rate in Asexual Populations," Science, vol. 283, pp. 404–406 (1999).

(List continued on next page.)

*Primary Examiner*—Remy Yucel
(74) *Attorney, Agent, or Firm*—Genencor International

(57) ABSTRACT

The present invention provides methods for directing the evolution of microorganisms comprising the use of mutator genes and growth under conditions of selective pressure. The method discloses mutator genes which can be used in the methods of the present invention and provides ATCC deposits which exemplify the evolved microorganisms produced by the methods.

38 Claims, 10 Drawing Sheets

OTHER PUBLICATIONS

Degenen et.al, "Conditional Mutator Gene in *Escherichia coli*: Is9lation, Mapping, and Effector Studies," *J. Bacteriol*, vol. 117, No. 2, pp. 477–487, (1974).

DeFrancesco et al., "The Interaction of DNA Polymerase III and the Product of the *Escherichia coli* Mutator Gene, mutD*," *The Journal of Biological Chemistry*, vol. 259 (9), pp. 5567–5573 (1984).

Dillon et al., "Spontaneous Mutation at the mtr Locus in Neurospora: The Molecular Spectrum in Wild–Type and a Mutator Strain," *Genetics*, vol. 138(1), pp. 61–74 (1994).

Eigen et al, "The Origin of Genetic Information: Viruses as Models," *Gene*, vol. 135, pp. 37–47 (1993).

Gineti, "*Bacillus subtillis* mutS mutL operon: identification, nucleotide sequence and mutagenesis," *Microbiology*, vol. 142 (Pt 8), pp. 2021–2029 (Aug. 1996).

Greener et al., "Strategies In Molecular Biology," vol. 7, pp. 32–34, (1994).

Hall, "Evolutionary Potential of the ebgA Gene," *Mol. Biol. Evol.*, vol. 12, No. 3, pp. 514–517 (1995).

Harder et al., "A Review Microbial Selection in Continuous Culture," vol. 43, pp. 1–24 (1977).

Heery et al., "Curing of a plasmid from *E. coli* using high–voltage electroporation," *Nucl. Acids. Res., E. coli*, vol. 17, p. 10131 (1989).

Horiuchi et al, "A New Conditional Lethal Mutator (dnaQ49) in *Escherichia coli* K12,"*Mol. Gen. Genetics*, vol. 163, pp. 277–283 (1978).

Inoue, "A Pseudomonas thrives in high concentrations of toluene," *Nature*, vol. 338, pp. 264–266 (1989).

Irving et al., "Affinity Maturation of Recombinant Antibodies Using *E. coli* Mutator Cells," *Immunotechnology*, vol. 2, pp. 127–143 (1996).

Isken et al, "Bacteria tolerant to organic solvents," *Extremophiles*, vol. 2 (3), pp. 229–238 (1998).

Kieboom et al., "Active Efflux of Organic Solvents by *Pseudomonas putida* S12 is Induced by Solvents," *J. of Bacteriology*, vol. 180(24), pp. 6769–6772 (1998).

Macdonald et al., "Microsatellite Instability and Loss of Heterozygosity at DNA Mismatch Repair Gene Loci occurs During Hepatic Carcinogenesis," *Heptology*, vol. 28(1), pp. 90–97 (1998).

Maki et al., "Structure and expression of the dnaQ mutator and the RNase H genes of *Escherichia coli*: Overlap of the promoter regions," *Proc. Natl. Acad. Sci.*, U.S.A. vol. 80, pp. 7137–7141 (1983).

Mao et al., "Proliferation of Mutators in A Cell Population," *Journal of Bacteriology*, V. 179 (2), pp. 417–422 (1997).

Maruyama et al., "A Dominant (mutD5) and a Recessive (dnaQ49) Mutator of *Escherichia coli.,"Journal of Molecular Biology*, vol. 167, pp. 757–771 (1983).

Miller, J.H., "A Short Course in Bacterial Genetics," *Cold Spring Harbor Lab Press*, pp. 110–113 (1992).

Miller, "Experiments in Molecular Genetics," Episomes, *E. Coli*, Acridine *Orange Molecular Genetics*, p. 140 (1972).

Pham et.al, "The Base Substitution and Frameshift Fidelity of *Escherichia coli* DNA Polymerase III Holoenzyme in Vitro*," *J. of Biol. Chem.*, vol. 273(36), pp. 23575–23584 (1998).

Pinkart et.al, "Phospholipid Biosynthesis and Solvent Tolerance in *Pseudomonas putida* Strains," *J. Bacteriol*, vol. 179(13), pp. 4129–4226 (1997).

Priebe et al., "Nucleotide Sequence of the hexA Gene for DNA Mismatch Repair in *Streptococcus pneumoniae* and Homology of hexA to mutS of *Escherichia coli* and *Salmonella typhimurium,*" *J. Bacteriol*, vol. 170(1), pp. 190–196 (1988).

Prudhomme et al., "Mismatch Repair Genes of *Streptococcus pneumoniae*: HexA Confers a Mutator Phenotype in *Escherichia coli* by Negative Complementation," *J. Bacteriol.*; vol. 173(22), (1991).

Prudhomme et al., "Nucleotide Sequence of the *Streptococcus pneumoniae* hexB Mismatch Repair Gene: Homology of HexB to MutL of *Salmonella typhimurium* and to PMS1 of *Saccharomyces cerevisiae*," J. Bacteriology, vol. 171 (10), pp. 5332–5338 (1989).

Ramos, et al., "Mechanisms for Solvent Tolerance in Bacteria," *J. Biol. Chem,.* vol. 272(7), pp. 3887–3890 (1997).

Schaaper, "An *Escherichia coli* dnaE Mutation with Suppressor Activity toward Mutator mutD3," *Journal of Bacteriology*, vol. 174(6), pp. 1974–1982 (1992).

Schaaper, "Mechanisms of mutagenesis in the *Escherichia coli* mutator mutD5: Role of DNA mismatch repair,"*PNAS*, vol. 85, pp. 8126–8130 (1988).

Sniegowski et.al, "Evolution of high mutation rates in experimental populations of *E. coli*," *Nature*, vol. 387, pp. 703–705 (1997).

Snyder et.al, "Molecular genetics of bacteria," *American Society for Microbiology*, chap. 3: pp. 85–89 (1997).

Taddei et.al, "Role of mutator alleles in adaptive evolution," *Nature*, vol. 387, pp. 700–702 (1997).

Takano et al., "Structure and function of dnaQ and mutD mutators of *Escherichia coli*," *Mol. Gen. Genet.*, vol. 205(1), pp. 9–13 (1986).

Trobner et.al, "Selection against hypermutability in *Escherichia coli* during long term evolution," *Mol. Gen. Genet*, vol. 198, pp. 177–178 (1984).

Weber et al., "Adaptation of *pseudomonas putida* S12 to High Concentrations of Styrene and Other Organic Solvents," *Appl. Environ. Microbiol*, vol. 59(10), pp. 3502–3504) (1993).

Yomano, "Isolation and characterization of ethanol–tolerant mutants of *Escherichia coli* KO11 for fuel ethanol production," *J. Ind. Microgiol. Biotechnol.* vol. 20(2): pp. 132–138 (1998).

* cited by examiner

ATGACCGCTATGAGCACTGCAATTACACGCCAGATCGTTCTCGATACCGAAACCACCGGTATGAACCAGATTGGT 75
 M  T  A  M  S  T  A  I  T  R  Q  I  V  L  D  T  E  T  T  G  M  N  Q  I  G
                           —————————————— mutD ——————————————

GCGCACTATGAAGGCCACAAGATCATTGAGATCATTGGTGCCGTTGAAGTGGTGAACCGTCGCCTGACGGCAATAAC 150
 A  H  Y  E  G  H  K  I  I  E  I  G  A  V  E  V  V  N  R  R  L  T  G  N  N
————————————————————————————————— mutD —————————————————————————————————

TTCCATGTTTATCTCAAACCCGATCGGCTGGTGGATCCGGAAGCCTTTGGCGTACATGGTATTGCCGATGAATTT 225
 F  H  V  Y  L  K  P  D  R  L  V  D  P  E  A  F  G  V  H  G  I  A  D  E  F
————————————————————————————————— mutD —————————————————————————————————

TTGCTCGATAAGCCCACGTTTGCCGAAGTAGCCGATGAGTTCATGGACTATATTCGGGCGGAGTTGGTGATC 300
 L  L  D  K  P  T  F  A  E  V  A  D  E  F  M  D  Y  I  R  G  A  E  L  V  I
————————————————————————————————— mutD —————————————————————————————————

CATAACGCAGCCGTTCGATATCGGCTTTATGGACTACGAGTTTTCGTTGCTTAAGCGCGATATTCCGAAGACCAAT 375
 H  N  A  A  F  D  I  G  F  M  D  Y  E  F  S  L  L  K  R  D  I  P  K  T  N
————————————————————————————————— mutD —————————————————————————————————

FIG._1A

```
ACTTTCTGTAAGGTCACCGATAGCCTTGCGGGTGTGGCGAGGAAAATGTTTCCCGGTAAGGCGCAACAGCCTCGATGCG  450
         |---------------------------------- mutD ----------------------------------|
          T  F  C  K  V  T  D  S  L  A  V  A  R  K  M  F  P  G  K  R  N  S  L  D  A TTATGTGCTCGCTACGAAATAGATAACAGTAAACGAACGCTGCACGGGCATTACTCGATGCCCAGATCCTTGCG  525
 |---------------------------------- mutD ----------------------------------|
  L  C  A  R  Y  E  I  D  N  S  K  R  T  L  H  G  A  L  L  D  A  Q  I  L  A GAAGTTTATCTGGCGATGACCGGTGGTCAAACGTCGATGGCTTTTGCGATGGAAGGAGAGACACAACAGCAACAA  600
 |---------------------------------- mutD ----------------------------------|
  E  V  Y  L  A  M  T  G  G  Q  T  S  M  A  F  A  M  E  G  E  T  Q  Q  Q  Q GGTGAAGCAACAATTCAGCGCATTGTACGTCAGGCAAGTAAGTTACGCGTTGTTTTTGCGACAGATGAAGAGATT  675
 |---------------------------------- mutD ----------------------------------|
  G  E  A  T  I  Q  R  I  V  R  Q  A  S  K  L  R  V  V  F  A  T  D  E  E  I GCAGCTCATGAAGCCCGTCTCGATCTGGTTCAGAAGAAAGGCGGAAGTTGCCTCTGGCGAGCATAA  741
 |---------------------------- mutD ----------------------------|
  A  A  H  E  A  R  L  D  L  V  Q  K  K  G  G  S  C  L  W  R  A
```

FIG._1B

```
                    10                  20                  30                  40                  50                  60
               ┌─────────┬─────────┬─────────┬─────────┬─────────┬─────────┐
        10     A T G A G C T A T C G T T T G A T T A T C T G G T T C T T T G A A C T T C T T T T G G C C C C G G G C G C C    Eb_429T.dna
        10     A T G A G C T A T C G T T T G A T T A T C T G G T T C T T T G A A C T T C T T T T G G C C C C G G G C G C C    Eb_GEBT.dna 70                  80                  90                 100                 110                 120
               ┌─────────┬─────────┬─────────┬─────────┬─────────┬─────────┐
        70     G T T T C T G T T G G C C A G C G C C T G C C A G C T G C T G G G G G G T A A A A A A G C C C C T G C T G A C C    Eb_429T.dna
        70     G T T T C T G T T G G C C A G C G C C T G C C A G C T G C T G G G G G G T A A A A A A G C C C C T G C T G A C C    Eb_GEBT.dna 130                 140                 150                 160                 170                 180
               ┌─────────┬─────────┬─────────┬─────────┬─────────┬─────────┐
       130     G A T A A G G G C C T G C G C G C C A T T A A A G A C G G T G C T G T C G A T C A G A C C G T G A A G C A C C T G A A A    Eb_429T.dna
       130     G A T A A G G G C C T G C G C G C C A T T A A A G A C G G T G C T G T C G A T C A G A C C G T G A A G C A C C T G A A A    Eb_GEBT.dna 190                 200                 210                 220                 230                 240
               ┌─────────┬─────────┬─────────┬─────────┬─────────┬─────────┐
       190     G C C G C C G G T A T T G A G G T G G T C A T T T T T C G A C G G G G T G C T G A G C C C G A A A G A C A C C A A C    Eb_429T.dna
       190     G C C G C C G G T A T T G A G G T G G T C A T T T T T C G A C G G G G T G C T G A G C C C G A A A G A C A C C A A C    Eb_GEBT.dna 250                 260                 270                 280                 290                 300
               ┌─────────┬─────────┬─────────┬─────────┬─────────┬─────────┐
       250     G T G C T C G A C G G C C C T G G C C A T G T T C C G T A A A G A G C A G T G C G A C A T G A T A A T C A C C G T C G G C    Eb_429T.dna
       250     G T G C T C G A C G G C C C T G G C C A T G T T C C G T A A A G A G C A G T G C G A C A T G A T A A T C A C C G T C G G C    Eb_GEBT.dna
```

```
     610                                                     660
610  A C C C A C G C G G T A G A G G C C T A T A T C T C C A A A G A C G C C A A C C C G G T T A C C G A T G C C T T C T G C T   Eb_429T.dna
610  A C C C A C G C G G T A G A G G C C T A T A T C T C C A A A G A C G C C A A C C C G G T T A C C G A T G C C T T C T G C T   Eb_GEBT.dna 670                                                     720
670  A T T C A G G C C A T C A A A A C T G A T T G C C A C C A A C T T G C G C C A G G C C C G T C G C C C C T G G G G A C C A A C   Eb_429T.dna
670  A T T C A G G C C A T C A A A A C T G A T T G C C A C C A A C T T G C G C C A G G C C C G T C G C C C C T G G G G A C C A A C   Eb_GEBT.dna 730                                                     780
730  C T C A A A G C C C G T G A A A A C A T G G G C C C T G C C C T C T C T G C T G G C C C T T T A A C A A C   Eb_429T.dna
730  C T C A A A G C C C G T G A A A A C A T G G G C C C T G C C C T C T C T G C T G G C C C T T T A A C A A C   Eb_GEBT.dna 790                                                     840
790  G C C A A C C T G G G C T A T G T T C A C G C C A T G G C T C A C C A G C T G G G C G G C C C T G T A C G A C A T G G C C   Eb_429T.dna
790  G C C A A C C T G G G C T A T G T T C A C G C C A T G G C T C A C C A G C T G G G C G G C C C T G T A C G A C A T G G C C   Eb_GEBT.dna 850                                                     900
850  C A C G G G G T G G C G A A C G C G G T C C T G C C C C C A T G T C T G C C G C T A T A A C C T G A T T G C C A A C   Eb_429T.dna
850  C A C G G G G T G G C G A A C G C G G T C C T G C C C C C A T G T C T G C C G C T A T A A C C T G A T T G C C A A C   Eb_GEBT.dna
```

*FIG._2C*

```
           910         920         930         940         950         960
            |           |           |           |           |           |
     910  C C G G A A A A A T T T G C C G A T A T C G C C A C C T T T A T G G G G A A A A C A C C G G T C T T T C C A C C   Eb_429T.dna
          C C G G A A A A A T T T G C C G A T A T C G C C A C C T T T A T G G G G A A A A C A C C A C C G G T C T T T C C A C C   Eb_GEBT.dna 970         980         990        1000        1010        1020
            |           |           |           |           |           |
     970  A T G G A C G C C A G C G G A G C T G G C C A T C A G C G C C A T T G C C C G T C T G T C T A A A G A T G T C G G G A T C   Eb_429T.dna
          A T G G A C G C C A G C G G A G C T G G C C A T C A G C G C C A T T G C C C G T C T G T C T A A A G A T G T C G G G A T C   Eb_GEBT.dna 1030        1040        1050        1060        1070        1080
            |           |           |           |           |           |
    1030  C C G C A G C A C C T G C G T G A A C T G G G G G T A A A A G A G G C C G A C T T C C C G T A C A T G G C A G A A A T G   Eb_429T.dna
          C C G C A G C A C C T G C G T G A A C T G G G G G T A A A A G A G G C C G A C T T C C C G T A C A T G G C A G A A A T G   Eb_GEBT.dna 1090        1100        1110        1120        1130        1140
            |           |           |           |           |           |
    1090  G C C C T G A A A G A C G G C A A C G C C C T T C T C T A A C C C G C A A A G G G A A C G A A A A A G A G A T T G C C   Eb_429T.dna
          G C C C T G A A A G A C G G C A A C G C C C T T C T C T A A C C C G C A A A G G G A A C G A A A A A G A G A T T G C C   Eb_GEBT.dna 1150        1160        1170
            |           |           |
    1150  G A C A T T T T C C G C C A G G C A T T C T G A   Eb_429T.dna
          G A C A T T T T C C G C C A G G C A T T C T G A   Eb_GEBT.dna
```

Decoration 'Decoration #1': Shade (with solid black) residues that differ from the Consensus.

*FIG._2D*

```
 10                                                           100
  |---|---|---|---|---|---|---|---|---|
10  M S Y R M F D Y L V P N V N F F G P G A V S V V G Q R C Q L L G G K K A L L V T   Eb_429T.dna
10  M S Y R M F D Y L V P N V N F F G P G A V S V V G Q R C Q L L G G K K A L L V T   Eb_GEBT.dna 130                                                          220
      |---|---|---|---|---|---|---|---|---|
130  D K G L R A I K D G A V D Q T V K H L K A A G I E V V I F D G V E P N P K D T N   Eb_429T.dna
130  D K G L R A I K D G A V D Q T V K H L K A A G I E V V I F D G V E P N P K D T N   Eb_GEBT.dna 250                                                          340
      |---|---|---|---|---|---|---|---|---|
250  V L D G L A M F R K E Q C D M I I T V G G G S P H D C G K G I G I A A T H P G D   Eb_429T.dna
250  V L D G L A M F R K E Q C D M I I T V G G G S P L D C G K G I G I A A T H P G D   Eb_GEBT.dna 370                                                          460
      |---|---|---|---|---|---|---|---|---|
370  L Y S Y A G I E T L T N P L P P I I A V N T T A G T A S E V T R H C V L T N T K   Eb_429T.dna
370  L Y S Y A G I E T L T N P L P P I I A V N T T A G T A S E V T R H C V L T N T K   Eb_GEBT.dna 490                                                          580
      |---|---|---|---|---|---|---|---|---|
490  T K V K F V I V S W R N L P S V S I N D P L L M I G K P A G L T A A T G M D A L   Eb_429T.dna
490  T K V K F V I V S W R N L P S V S I N D P L L M I G K P A G L T A A T G M D A L   Eb_GEBT.dna
```

FIG._3A

```
     610                  640                670                700
610  T H A V E A Y I S K D A N P V T D A S A I Q A I K L I A T N L R Q A V A L G T N   Eb_429T.dna
610  T H A V E A Y I S K D A N P V T D A S A I Q A I K L I A T N L R Q A V A L G T N   Eb_GEBT.dna 730                  760                790                820
730  L K A R E N M A C A S L L A G M A F N N A N L G Y V H A M A H Q L G G L Y D M A   Eb_429T.dna
730  L K A R E N M A C A S L L A G M A F N N A N L G Y V H A M A H Q L G G L Y D M A   Eb_GEBT.dna 850                  880                910                940
850  H G V A N A V L L P H V C R Y N L I A N P E K F A D I A T F M G E N T T G L S T   Eb_429T.dna
850  H G V A N A V L L P H V C R Y N L I A N P E K F A D I A T F M G E N T T G L S T   Eb_GEBT.dna 970                  1000               1030               1060
970  M D A A E L A I S A I A R L S K D V G I P Q H L R E L G V K E A D F P Y M A E M   Eb_429T.dna
970  M D A A E L A I S A I A R L S K D V G I P Q H L R E L G V K E A D F P Y M A E M   Eb_GEBT.dna 1090                 1120               1150
1090 A L K D G N A F S N P R K G N E K E I A D I F R Q A F                             Eb_429T.dna
1090 A L K D G N A F S N P R K G N E K E I A D I F R Q A F                             Eb_GEBT.dna
```

Decoration 'Decoration #1': Shade (with solid black) residues that differ from the Consensus.

*FIG._3B*

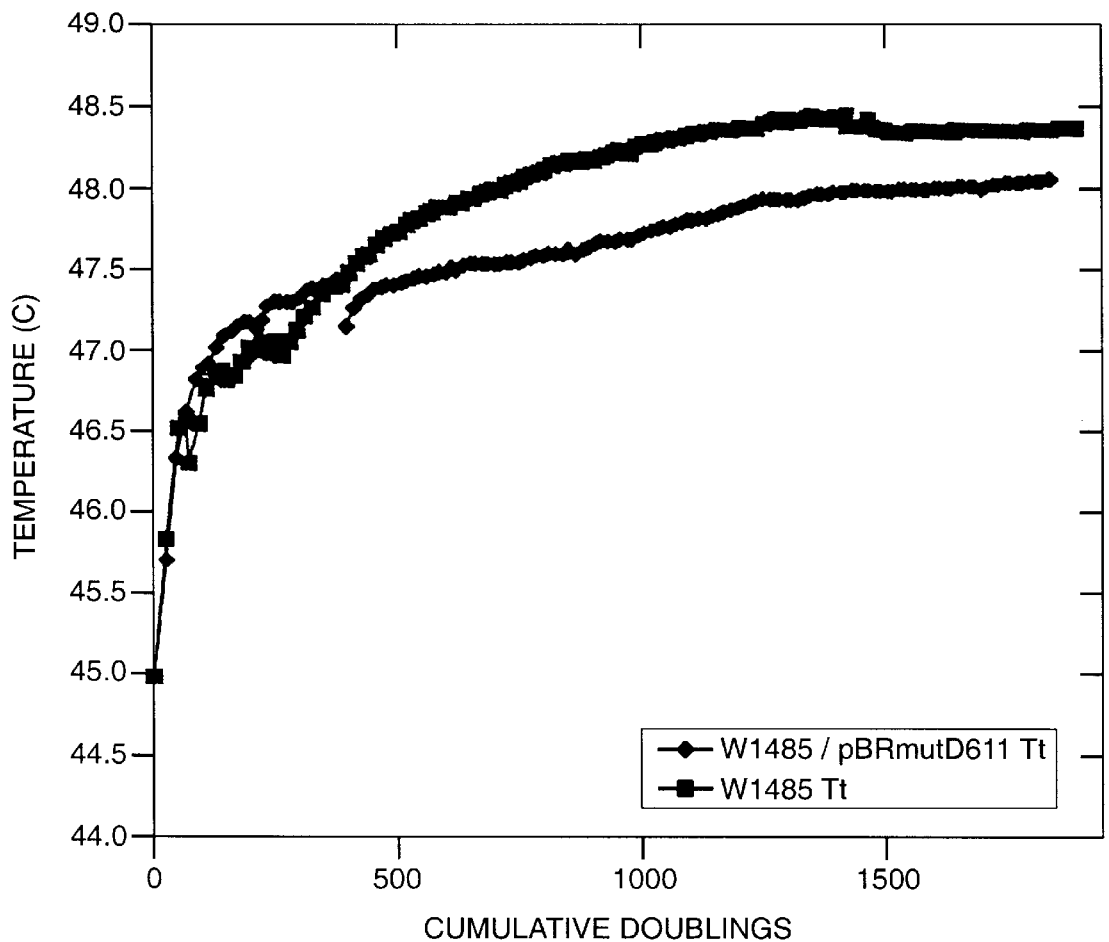
FIG._4

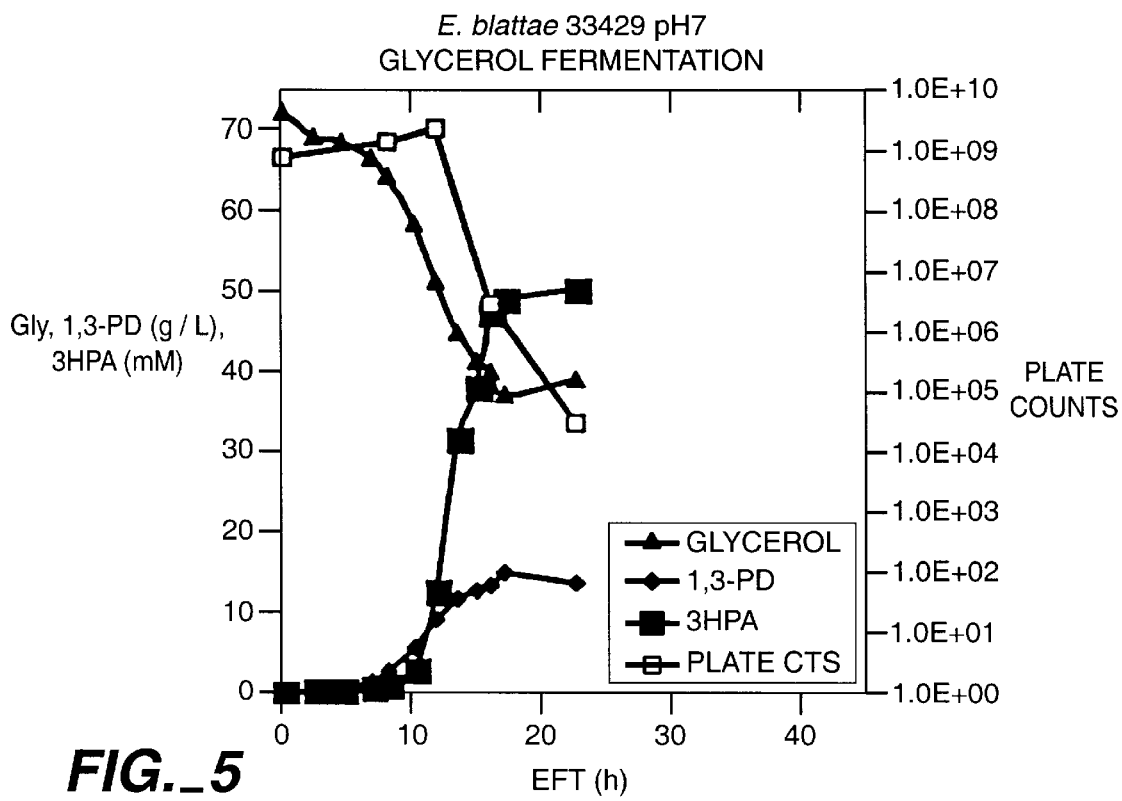
FIG._5
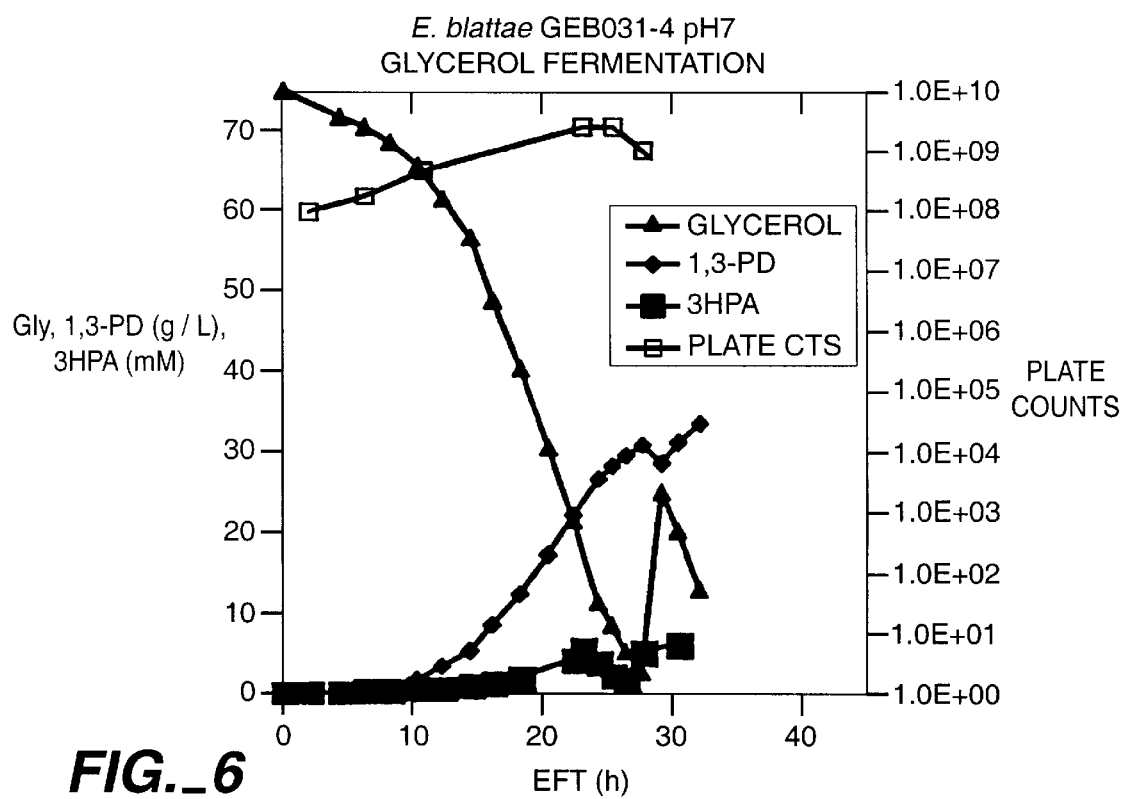
FIG._6

SEQUENCE LISTING

<160> NUMBER OF SEQ ID NOS: 15

<210> SEQ ID NO 1
<211> LENGTH: 741
<212> TYPE: DNA
<213> ORGANISM: E. coli

<400> SEQUENCE: 1

```
atgaccgcta tgagcactgc aattacacgc cagatcgttc tcgataccga aaccaccggt      60
atgaaccaga ttggtgcgca ctatgaaggc cacaagatca ttgagattgg tgccgttgaa     120
gtggtgaacc gtcgcctgac gggcaataac ttccatgttt atctcaaacc cgatcggctg     180
gtggatccgg aagcctttgg cgtacatggt attgccgatg aatttttgct cgataagccc     240
acgtttgccg aagtagccga tgagttcatg gactatattc gcggcgcgga gttggtgatc     300
cataacgcag cgttcgatat cggctttatg gactacgagt tttcgttgct taagcgcgat     360
attccgaaga ccaatacttt ctgtaaggtc accgatagcc ttgcggtggc gaggaaaatg     420
tttcccggta agcgcaacag cctcgatgcg ttatgtgctc gctacgaaat agataacagt     480
aaacgaacgc tgcacggggc attactcgat gcccagatcc ttgcggaagt ttatctggcg     540
atgaccggtg gtcaaacgtc gatggctttt gcgatggaag gagagacaca acagcaacaa     600
ggtgaagcaa caattcagcg cattgtacgt caggcaagta agttacgcgt tgtttttgcg     660
acagatgaag agattgcagc tcatgaagcc cgtctcgatc tggtgcagaa gaaaggcgga     720
agttgcctct ggcgagcata a                                               741
```

<210> SEQ ID NO 2
<211> LENGTH: 246
<212> TYPE: PRT
<213> ORGANISM: E. coli

<400> SEQUENCE: 2

```
Met Thr Ala Met Ser Thr Ala Ile Thr Arg Gln Ile Val Leu Asp Thr
 1               5                  10                  15
Glu Thr Thr Gly Met Asn Gln Ile Gly Ala His Tyr Glu Gly His Lys
            20                  25                  30
Ile Ile Glu Ile Gly Ala Val Glu Val Val Asn Arg Arg Leu Thr Gly
        35                  40                  45
Asn Asn Phe His Val Tyr Leu Lys Pro Asp Arg Leu Val Asp Pro Glu
    50                  55                  60
Ala Phe Gly Val His Gly Ile Ala Asp Glu Phe Leu Leu Asp Lys Pro
65                  70                  75                  80
Thr Phe Ala Glu Val Ala Asp Glu Phe Met Asp Tyr Ile Arg Gly Ala
                85                  90                  95
Glu Leu Val Ile His Asn Ala Ala Phe Asp Ile Gly Phe Met Asp Tyr
               100                 105                 110
Glu Phe Ser Leu Leu Lys Arg Asp Ile Pro Lys Thr Asn Thr Phe Cys
           115                 120                 125
```

Lys Val Thr Asp Ser Leu Ala Val Ala Arg Lys Met Phe Pro Gly Lys
    130                 135                 140

Arg Asn Ser Leu Asp Ala Leu Cys Ala Arg Tyr Glu Ile Asp Asn Ser
145                 150                 155                 160

Lys Arg Thr Leu His Gly Ala Leu Leu Asp Ala Gln Ile Leu Ala Glu
                165                 170                 175

Val Tyr Leu Ala Met Thr Gly Gly Gln Thr Ser Met Ala Phe Ala Met
            180                 185                 190

Glu Gly Glu Thr Gln Gln Gln Gly Glu Ala Thr Ile Gln Arg Ile
        195                 200                 205

Val Arg Gln Ala Ser Lys Leu Arg Val Val Phe Ala Thr Asp Glu Glu
    210                 215                 220

Ile Ala Ala His Glu Ala Arg Leu Asp Leu Val Gln Lys Lys Gly Gly
225                 230                 235                 240

Ser Cys Leu Trp Arg Ala
            245

<210> SEQ ID NO 3
<211> LENGTH: 1164
<212> TYPE: DNA
<213> ORGANISM: E. blatte

<400> SEQUENCE: 3

```
atgagctatc gtatgtttga ttatctggtt ccaaatgtga acttctttgg cccgggcgcc     60
gtttctgttg ttggccagcg ctgccagctg ctgggggta aaaaagccct gctggtgacc    120
gataagggcc tgcgcgccat taagacggt gctgtcgatc agaccgtgaa gcacctgaaa    180
gccgccggta ttgaggtggt cattttcgac ggggtcgagc cgaacccgaa agacaccaac    240
gtgctcgacg gcctggccat gttccgtaaa gagcagtgcg acatgataat caccgtcggc    300
ggcggcagcc cgcacgactg cggtaaaggc attggtattg cggccaccca cccgggtgat    360
ctgtacagct atgccggtat cgaaacactc accaacccgc tgccgcccat tattgcggtc    420
aacaccaccg ccgggaccgc cagcgaagtc acccgccact gcgtgctgac taacaccaaa    480
accaaagtaa aatttgtgat tgtcagctgg cgcaacctgc cttccgtctc cattaacgat    540
ccgctgctga tgatcggcaa gcccgccggg ctgaccgccg ccaccggtat ggatgccctg    600
acccacgcgg tagaggccta tctccaaa gacgccaacc cggttaccga tgcctctgct    660
attcaggcca tcaaactgat tgccaccaac ttgcgccagg ccgtcgccct ggggaccaac    720
ctcaaagccc gtgaaaacat ggcctgcgcc tctctgctgg ccgggatggc ctttaacaac    780
gccaacctgg gctatgttca cgccatggct caccagctgg gcggcctgta cgacatggcc    840
cacggggtgg cgaacgcggt cctgctgccc catgtctgcc gctataacct gattgccaac    900
ccggaaaaat tgccgatat cgccaccttt atggggaaa acaccaccgg tctttccacc    960
atggacgcag cggagctggc catcagcgcc attgcccgtc tgtctaaaga tgtcgggatc   1020
ccgcagcacc tgcgtgaact gggggtaaaa gaggccgact tcccgtacat ggcagaaatg   1080
gccctgaaag acggcaacgc cttctctaac ccgcgcaaag gaacgaaaa agagattgcc   1140
gacatttttcc gccaggcatt ctga                                        1164
```

<210> SEQ ID NO 4
<211> LENGTH: 387
<212> TYPE: PRT
<213> ORGANISM: E. blatte

```
<400> SEQUENCE: 4

Met Ser Tyr Arg Met Phe Asp Tyr Leu Val Pro Asn Val Asn Phe Phe
1               5                   10                  15

Gly Pro Gly Ala Val Ser Val Val Gly Gln Arg Cys Gln Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Gln Thr Val Lys His Leu Lys Ala Ala Gly Ile
    50                  55                  60

Glu Val Val Ile Phe Asp Gly Val Glu Pro Asn Pro Lys Asp Thr Asn
65                  70                  75                  80

Val Leu Asp Gly Leu Ala Met Phe Arg Lys Glu Gln Cys Asp Met Ile
                85                  90                  95

Ile Thr Val Gly Gly Gly Ser Pro His Asp Cys Gly Lys Gly Ile Gly
            100                 105                 110

Ile Ala Ala Thr His Pro Gly Asp Leu Tyr Ser Tyr Ala Gly Ile Glu
        115                 120                 125

Thr Leu Thr Asn Pro Leu Pro Pro Ile Ile Ala Val Asn Thr Thr Ala
    130                 135                 140

Gly Thr Ala Ser Glu Val Thr Arg His Cys Val Leu Thr Asn Thr Lys
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Gly Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ser Ala Ile Gln Ala Ile
210                 215                 220

Lys Leu Ile Ala Thr Asn Leu Arg Gln Ala Val Ala Leu Gly Thr Asn
225                 230                 235                 240

Leu Lys Ala Arg Glu Asn Met Ala Cys Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Ala His Gly Val Ala Asn Ala Val Leu
        275                 280                 285

Leu Pro His Val Cys Arg Tyr Asn Leu Ile Ala Asn Pro Glu Lys Phe
    290                 295                 300

Ala Asp Ile Ala Thr Phe Met Gly Glu Asn Thr Thr Gly Leu Ser Thr
305                 310                 315                 320

Met Asp Ala Ala Glu Leu Ala Ile Ser Ala Ile Ala Arg Leu Ser Lys
                325                 330                 335

Asp Val Gly Ile Pro Gln His Leu Arg Glu Leu Gly Val Lys Glu Ala
            340                 345                 350

Asp Phe Pro Tyr Met Ala Glu Met Ala Leu Lys Asp Gly Asn Ala Phe
        355                 360                 365

Ser Asn Pro Arg Lys Gly Asn Glu Lys Glu Ile Ala Asp Ile Phe Arg
    370                 375                 380

Gln Ala Phe
385

<210> SEQ ID NO 5
```

```
<211> LENGTH: 12
<212> TYPE: DNA
<213> ORGANISM: Artificial Sequence
<220> FEATURE:
<223> OTHER INFORMATION: wild type mutD gene

<400> SEQUENCE: 5
atgaccgcta tg                                                          12

<210> SEQ ID NO 6
<211> LENGTH: 11
<212> TYPE: DNA
<213> ORGANISM: Artificial Sequence
<220> FEATURE:
<223> OTHER INFORMATION: pOS100 mutD mutated gene

<400> SEQUENCE: 6
ttgacgcttt g                                                           11

<210> SEQ ID NO 7
<211> LENGTH: 12
<212> TYPE: DNA
<213> ORGANISM: Artificial Sequence
<220> FEATURE:
<223> OTHER INFORMATION: pOS101 mutD mutated gene

<400> SEQUENCE: 7
gtgaccgctg tg                                                          12

<210> SEQ ID NO 8
<211> LENGTH: 11
<212> TYPE: DNA
<213> ORGANISM: Artificial Sequence
<220> FEATURE:
<223> OTHER INFORMATION: pOS102 mutD mutated gene

<400> SEQUENCE: 8
gtgccgctgt g                                                           11

<210> SEQ ID NO 9
<211> LENGTH: 12
<212> TYPE: DNA
<213> ORGANISM: Artificial Sequence
<220> FEATURE:
<223> OTHER INFORMATION: pOS104 mutD mutated gene

<400> SEQUENCE: 9
ttgaccgctt tg                                                          12

<210> SEQ ID NO 10
<211> LENGTH: 55
<212> TYPE: DNA
<213> ORGANISM: Artificial Sequence
<220> FEATURE:
<223> OTHER INFORMATION: pOS105 mutD mutated gene

<400> SEQUENCE: 10
gtgaccgctg tgagcacttg caattacacg ccagatcgtt ctcgataccg aaatc           55

<210> SEQ ID NO 11
<211> LENGTH: 11
<212> TYPE: DNA
<213> ORGANISM: Artificial Sequence
<220> FEATURE:
<223> OTHER INFORMATION: pOS106 mutD mutated gene

<400> SEQUENCE: 11
```

```
gtgaccgctt g                                                          11

<210> SEQ ID NO 12
<211> LENGTH: 28
<212> TYPE: DNA
<213> ORGANISM: Artificial Sequence
<220> FEATURE:
<223> OTHER INFORMATION: primer

<400> SEQUENCE: 12
cgcctccagc gcgacaatag cggccatc                                        28

<210> SEQ ID NO 13
<211> LENGTH: 27
<212> TYPE: DNA
<213> ORGANISM: Artificial Sequence
<220> FEATURE:
<223> OTHER INFORMATION: primer

<400> SEQUENCE: 13
ccgactgaac taccgctccg cgttgtg                                         27

<210> SEQ ID NO 14
<211> LENGTH: 36
<212> TYPE: DNA
<213> ORGANISM: Artificial Sequence
<220> FEATURE:
<223> OTHER INFORMATION: primer

<400> SEQUENCE: 14
tctgatacgg gatcctcaga atgcctggcg gaaaat                               36

<210> SEQ ID NO 15
<211> LENGTH: 42
<212> TYPE: DNA
<213> ORGANISM: Artificial Sequence
<220> FEATURE:
<223> OTHER INFORMATION: primer

<400> SEQUENCE: 15
gcgccgtcta gaattatgag ctatcgtatg tttgattatc tg                        42
```

DIRECTED EVOLUTION OF MICROORGANISMS

FIELD OF THE INVENTION

The present invention relates to methods for directing the evolution of microorganisms using mutator genes. Such methods provide a pool of microbial genetic diversity advantageous for industrial application, such as for the industrial production of heterologous proteins, such as hormones, growth factors and enzymes, and the biocatalytic production of chemicals, vitamins, amino acids and dyes.

BACKGROUND OF THE INVENTION

The industrial applicability of microorganisms is restricted by their physiological limits set by solvent, pH, various solutes, salts and temperature. Organic solvents are generally toxic to microorganisms even at low concentrations. The toxicity of solvents significantly limits use of microorganisms in industrial biotechnology for production of specialty chemicals and for bioremediation applications. Solvent molecules incorporate into bacterial membranes and disrupt membrane structure (Isken and Bont, 1998, *Extremophiles* 2(3): 229–238); (Pinkart and White, 1997, *J. Bacteriol.* 179(13): 4219–4226); (Ramos, Duque et al., 1997, "*J. Biol. Chem.* 272(7): 3887–3890); (Alexandre, Rousseaux et al., 1994, *FEMS Microbiol, Lett*, 124(1): 17–22); and Kieboom, Dennis et al., 1998, *J. of Bacteriology* 180(24): 6769–6772). Classic strain improvement methods including UV and chemical mutagenesis have been applied for selection of more tolerant strains (Miller, J., "A Short Course In Bacterial Genetics," Cold Spring Harbor Laboratory Press, 1992). A number of studies have been dedicated to identification and isolation of solvent tolerant mutants among various bacterial strains. Spontaneous *E. coli* solvent tolerant mutants and mutants isolated in the process of 1-methyl-3-nitrosoguanidine (NTG) mutagenesis were obtained from strain K-12 (Aono, Aibe et al., 1991 *Agric. Biol. Chem* 55(7): 1935–1938). The mutants could grow in the presence of diphenylether, n-hexane, propylbenzene, cyclohexane, n-pentane, p-xylene. Various Pseudomonas strains were able to adapt and to grow in a toluene-water two-phase system (Inoue and Horikoshi, 1989, *Nature* 338: 264–266), with p-xylene (Cruden, Wolfram et al., 1992, *Appl. Environ. Microbiol.* 58(9): 2723–2729), styrene and other organic solvents (Weber, Ooijkaas et al., 1993, *Appl. Environ. Microbiol.* 59(10): 3502–3504), (de Bont 1998, *Trends in Biotechnology* 16: 493–499). Yomano et al. isolated ethanol tolerant mutants which increased tolerance from 35 g/l to 50 g/l during 32 consequent transfers (Yomano, York et al., 1998, *J. Ind. Microbiol. Biotechnol.* 20(2): 132–138). High temperature evolution using E.coli has been disclosed in the art (Bennett, 1990, *Nature*, Vol. 346, 79–81) however the fitness gain was low as compared to the parent.

Strains of *E. coli* that carry mutations in one of the DNA repair pathways have been described which have a higher random mutation rate than that of typical wild type strains (see, Miller supra, pp.193–211). As reported by Degenen and Cox (*J. Bacteriol.*, 1974, Vol. 117, No. 2, pp.477–487), an *E. coli* strain carrying a mutD5 allele demonstrates from 100 to 10,000 times the mutation rate of its wild type parent. Greener et al., "Strategies In Molecular Biology," 1994, Vol. 7, pp.32–34, disclosed a mutator strain that produces on average one mutation per 2000 bp after growth for about 30 doublings.

Microorganisms are used industrially to produce desired proteins, such as hormones, growth factors and enzymes and to produce chemicals, such as glycerol and 1,3 propanediol (WO 98/21340 published May 22, 1998 and U.S. Pat. No. 5,686,276 issued Nov. 11, 1997), vitamins, such as ascorbic acid intermediates (1985, *Science* 230:144–149), amino acids, and dyes, such as indigo (U.S. Pat. No. 4,520,103, issued May 28, 1985). In spite of advances in the art, there remains a need to improve the microorganisms and methods for producing such desired proteins, chemicals, amino acids and dyes.

SUMMARY OF THE INVENTION

The present invention relates generally to methods for directing the evolution of a microorganism, that is for directing desired genetic change in a microorganism in response to conditions of selective pressure. In one aspect, the present invention relates to methods for evolving microorganisms to grow under extreme conditions, such as at high temperature, under conditions of pH extremes, in the presence of solvents, and in the presence of high salt. In another aspect, the present invention relates to methods for evolving a microorganism comprising at least one nucleic acid encoding a desired protein or an enzyme in an enzymatic pathway to grow under desired conditions.

The present invention is based, in part, upon the finding that microrganisms such as wild-type *E.coli* and *E.blattae*, can be evolved into microorganisms capable of growing in the presence of high solvents, such as DMF and 1,3 propanediol, using methods described herein. The present invention is also based, in part, upon the finding that *E.coli* can be evolved into a microorganism capable of growing at elevated temperatures using methods described herein. The present invention is further based, in part, upon the identification of the optimal mutation rate for a microorganism and the discovery that the mutation rate can be controlled.

Accordingly, the present invention provides a method for preparing an evolved microorganism comprising the steps of culturing a microorganism comprising at least one heterologous mutator gene, for at least 20 doublings under conditions suitable for selection of an evolved microorganism, wherein said heterologous mutator gene generates a mutation rate of at least about 5 fold to about 100,000 fold relative to wild type, and restoring said evolved microorganism to a wild type mutation rate. In one embodiment, the microorganism further comprises at least one introduced nucleic acid encoding a heterologous protein, said protein(s) including, but not limited to hormones, enzymes, growth factors. In another embodiment, the enzyme includes, but is not limited to hydrolases, such as protease, esterase, lipase, phenol oxidase, permease, amylase, pullulanase, cellulase, glucose isomerase, laccase and protein disulfide isomerase. The present invention encompasses genetic changes in the microorganism as well as changes in the introduced nucleic acid.

In yet a further embodiment, the microorganism further comprises introduced nucleic acid encoding at least one enzyme necessary for an enzymatic pathway. In one embodiment, the introduced nucleic acid is heterologous to the microorganism; in another, the introduced nucleic acid is homologous to the microorganism. In a further embodiment, the enzyme is a reductase or a dehydrogenase and said enzymatic pathway is for the production of ascorbic acid or ascorbic acid intermediates. In an additional embodiment, the enzyme is glycerol dehydratase or 1,3-propanediol dehydrogenase and said enzymatic pathway is for the production of 1,3 propanediol, 1,3 propanediol precursors or 1,3 propanediol derivatives. In another embodiment, the enzyme is glycerol-3-phosphate dehydrogenase or glycerol-3-phosphate phosphatase and said pathway is for the production of glycerol and glycerol derivatives. In a further embodiment, the enzymatic pathway is for the production of amino acids, such as tryptophane or lysine or dyes, such as indigo.

In one embodiment of the present invention, the microorganism is cultured for between about 20 to about 100 doublings; in another embodiment, the microorganism is cultured for between about 100 to about 500 doublings; in yet another embodiment, the microorganism is cultured for between about 500 to about 2000 doublings and in a further embodiment, the microorganism is cultured for greater than 2000 doublings. In one embodiment, the mutator gene generates a mutation rate of at least about 5 fold to about 10,000 fold relative to wild type; in another embodiment, the mutator gene generates a mutation rate of a least about 5 fold to about 1000 fold and in another embodiment, the mutator gene generates a mutation rate of about 5 fold to about 100 fold over wild type.

In one embodiment, an evolved microorganism comprises from about 3 to about 1000 selected mutations in about 3 to about 500 genes and may further comprises from about 20 to about 100,000 neutral mutations. In one aspect, the mutations generated are non-specific and in another aspect, the mutations generated are specific.

In one embodiment of the present invention, the microorganism comprises a plasmid comprising the heterologous mutator gene and said step of restoring said evolved microorganism to a wild type mutation rate comprises curing the evolved microorganism of said plasmid. In another embodiment, the plasmid comprises a temperature sensitive origin of replication and the curing comprises growing the evolved microorganism at a restrictive temperature. In a further embodiment, the microorganism comprises at least one copy of the mutator gene in the chromosome and said step of restoring said evolved microorganism to a wild type mutation rate comprises excision or removal of said mutator gene from the host genome or the replacement of the mutator gene with a functional (non-mutator) allele of the same gene.

In one embodiment, the present invention comprises the use of at least one mutator gene to evolve a microorganism. In another embodiment, the mutator gene includes but is not limited to a mutD gene mutation, a mutT gene mutation, a mutY gene mutation, a mutM gene mutation, a mutH gene mutation, a mutL gene mutation, a mutS gene mutation or a mutU gene mutation and homologues of these DNA repair genes which have been mutated as long as the mutated gene has impaired proofreading function. In a further embodiment, the mutator gene comprises at least one of the mutD mutations disclosed herein in Table 1.

In one embodiment of the present invention, conditions suitable for selection include but are not limited to culturing said microorganism in the presence of at least one organic solvent, such as for example, alcohols, diols, hydrocarbon, mineral oil, mineral oil derived products, halogenated compounds and aromatic compounds; in the presence of high temperature, such as in the range of 42°–48° C.; in the presence of high salt, and in the presence of extreme pH conditions, such as alkaline or acidic conditions.

The present invention encompasses methods for evolving gram positive and gram negative microorganisms as well as yeast, fungus and eucaryotic cells including hybridomas. In one embodiment, the gram negative microorganism includes members of Enterobacteriaceae and in another embodiment comprises Eschericia and in another embodiment comprises E.coli and E.blatte.

In further embodiments of the present invention, the evolved microorganism includes E.coli having ATCC accession number PTA-91 and E.blattae having ATCC accession number PTA-92.

The present invention also provides expression vectors and host cells comprising a mutator gene and methods for producing such vectors and host cells.

BRIEF DESCRIPTION OF THE DRAWINGS

FIG. 1 shows the nucleic acid SEQ ID NO:1 and amino acid SEQ ID NO:2 sequence of the mutD gene. Illustrative examples of mutations of the mutD gene are provided.

FIG. 2 provides the nucleic acid SEQ ID NO:3 sequence for the enzyme 1,3-propanediol dehydrogenase (PDD).

FIG. 3 provides the amino acid SEQ ID NO:4 sequence for the enzyme 1,3-propanediol dehydrogenase (PDD).

FIG. 4 provides a time course for E.coli cultures subjected to directed evolution and selection under elevated temperature.

FIG. 5—Glycerol fermentation of E. blattae at pH 7.0. Culture conditions are described in the text. Plate counts were by serial dilution and performed in triplicate on Luria agar plates. Substrate and 0products were measured by HPLC.

FIG. 6—Glycerol fermentation of E. blattae strain GEB031-4 at pH 7.0. Culture conditions are described in the text. Plate counts were by serial dilution and performed in triplicate on Luria agar plates. Substrate and products were measured by HPLC.

DESCRIPTION OF THE MICROORGANISM DEPOSITS MADE UNDER THE BUDAPEST TREATY

Applicants have made the following biological deposits under the terms of the Budapest Treaty on the International Recognition of the Deposit of Micro-organisms for the Purposes of Patent Procedure:

| Depositor Identification Reference | International Depository Designation | Date of Deposit |
| --- | --- | --- |
| Escherichia coli MM294 derivative | ATCC PTA-91 | May 19, 1999 |
| Escherichia blattae 33429 derivative | ATCC PTA-92 | May 19, 1999 |

The ATCC is located at 10801 University Boulevard, Manassas, Va., 20110-2209.

DETAILED DESCRIPTION

Definitions

A mutation refers to any genetic change that occurs in the nucleic acid of a microorganism and may or may not reflect a phenotypic change within the microorganism. A mutation may comprise a single base pair change, deletion or insertion; a mutation may comprise a change, deletion or insertion in a large number of base pairs; a mutation may also comprise a change in a large region of DNA, such as through duplication or inversion.

When many possible different mutations in nucleic acid can give rise to a particular phenotype, the chance of mutation to that phenotype will be higher than in a situation where only a few types of mutations can give rise to a particular phenotype. As used herein the terms "wild-type mutation" and "spontaneous mutation" are used interchangeably. The rate of spontaneous mutation is defined as the probability of a mutation each time the genome is replicated or doubled. As used herein "mutation rate" is simultaneous with "frequency" and refers to the absolute number of mutations/doubling/base pair. As used herein, the term "relative rate" refers to the ratio of mutation rates of two strains, one of these is usually a wild type strain. Relative rate indicates how much more likely it is that a strain will undergo mutation as compared to the wild type strain. The frequency of spontaneous mutation of wild type *E. coli* (the *E.coli* genome has about 4.6×10$^6$ base pairs) is about 5×10$^{-10}$) mutations per base pair per doubling (see Drake, 1991). Doubling refers to the process of reproduction of at least part of a genome of an organism and usually involves reproduction by binary fission. As used herein, "doubling" encompasses the reproduction of nucleic acid within an microorganism achieved by any means.

As used herein, a "mutator strain" refers to a microorganism having a higher than naturally occurring rate of spontaneous mutation. As used herein, "mutator gene" refers to a DNA repair gene which comprises a mutation and which has impaired proof reading function. As used herein, the term "mutator plasmid" refers to a plasmid or expression vector or cassette comprising a mutator gene. Culturing a microorganism comprising a mutator gene will give rise to mutational events during genome replication. The present invention encompasses the use of any DNA repair genes comprising mutations as long as the mutated DNA repair gene is capable of introducing mutational events in a microorganisms genome or on a gene introduced into the microorganism. DNA repair genes include but are not limited to, mutD, mutT, mutY, mutM, mutH, mutL, mutS or mutU and homologues of these genes. A homologue as used herein refers to a functionally related DNA repair gene. In one embodiment, the mutator gene is a mutD gene (the epsilon subunit of DNA polymerase III, see Degnen et al., 1974, *J. Bacteriol.* 117:477–487) comprising mutations that provide an impaired proofreading function. In one embodiment disclosed herein, the mutD mutation is introduced into a microorganism on a plasmid. Illustrative embodiments of MutD mutations are disclosed herein in Table I. The mutD mutations impair proofreading function of the epsilon subunit of DNA polymerase III holoenzyme by significant decrease in the 3'–5' exonuclease activity (Takano et al., 1986, *Mol. Gen. Genet.* 205(1):9–13).

When referring to mutations or genetic changes in an evolved microorganism, "neutral mutation" refers to a mutation which has little or no measurable effect on the phenotype of an evolved strain under a given set of conditions. Examples of "neutral mutations" include, but are not limited to, silent mutations which do not lead to a change in the amino acid sequence of the encoded protein, mutations which affect proteins that are not essential for growth under a given set of culture conditions, and mutations in non-coding regions of the chromosome. In one illustrative embodiment herein, an *E.coli* strain evolved for high temperature was characterized as being auxotrophic for three amino acids (ie, were not able to grow in medium without Cys/Met, Asp/Asn, and Pro) indicating that there were at least three neutral mutations in the *E.coli* in addition to the mutations associated with growth at high temperature. The term "selected mutation" as used herein refers to those mutations which are associated with a phenotype of an evolved strain under a given set of conditions. Being associated with means that the mutation is directly or indirectly responsible for the improved or altered phenotype.

When referring to mutations or genetic changes in a host cell or microorganism, nonspecific refers to the changes in the host cell genome which occur randomly throughout the genome and which potentially can affect all bases and includes frameshifts. Non-specific mutations encompass changes in single base pairs as well as changes in a large number of base pairs as well as changes in large regions of DNA. For example, in one embodiment, an evolved microorganism which has been exposed to a MutD gene comprising mutations that impair the proof reading function will comprise random mutations at a rate of about 5–1000 times over wild type. In one illustrative embodiment of the method using a mutD mutation, the evolved strain had at least 3 random mutations. The present invention encompasses any rate of mutations that provides the desired phenotype. When referring to genetic changes in a host cell, specific mutation refers to mutations which can be characterized or which comprise definable genetic changes, such as A:T to C:G transversion characteristic of mutT mutations; G:C to T:A transversion characteristic of mutY and mutM mutations; A:T to G:C and G:C to A:T transitions and frameshifts characteristic of mutH, mutL, mutS, uvrD (mutU) mutations; G:C to T:A transversions characteristic of the mutYmutM double mutation (Miller et al., A Short Course in Bacterial Genetics, a Laboratory Manual and Handbook for *E.coli* and Related Bacteria).

When referring to a mutator gene, "heterologous" means that the gene is introduced into the cell via recombinant methods and is preferably introduced on a plasmid. The mutator gene may also be introduced into the microorganism genome through recombinant techniques. The mutator gene introduced into the microorganism may be a mutation of a naturally occurring DNA repair gene in the cell or may be foreign to the host microorganism. Referring to nucleic acid as being "introduced" into a microorganism means that the nucleic acid is put into the microorganism using standard molecular biology techniques. An introduced nucleic acid may be the same or different than nucleic acid naturally occurring in the microorganism.

As used herein the term "restoring to wild type mutation rate" refers to the process whereby a mutator gene is removed from an evolved microorganism thereby restoring the wild-type mutation rates. The present invention encompasses any process for removing the mutator gene from an evolved organism and includes but is not limited to curing the organism of a resident plasmid comprising the mutator gene or by excising or otherwise removing the mutator gene from the host genome such that normal DNA repair function is restored. Curing refers to methods for producing cells which are free of a plasmid comprising the mutator gene. A microorganism can be cured of any resident plasmid using techniques known to the skilled artisan.

Detailed Description

One of the basic tenants of inheritance is that mutations occur randomly and then are selected by the environment. Mutations that happen to confer a selective advantage on the organism are preferentially passed on to future generations. The present invention relates to methods for directing desired genetic change in a microorganism, ie directing the evolution of a microorganism, by exposing the microorganism to a mutator gene, selecting for acquisition of desired characteristics in the evolved microorganism, and curing the microorganism of the mutator gene, or otherwise removing the mutator gene, such that wild type mutation rates are restored.

I. Uses of the Invention

In one aspect of the present invention, the methods are used to evolve a microorganism to grow under extreme conditions, such as in the presence of elevated temperature, high solvent, altered pH or in the presence of high salt. In another aspect of the present invention, the methods are used to evolve microorganisms which comprise introduced nucleic acid encoding a heterologous protein or at least one enzyme in an enzymatic, ie biocatalytic pathway. Such commercially important proteins include hormones, growth factors and enzymes. Illustrative biocatalytic pathways include those disclosed in U.S. Pat. No. 5,686,276, issued Nov. 11, 1997, for the production of 1,3-propanediol and in 1985, Science 230:144–149 for the production of ascorbic acid intermediates.

Methods of the present invention are especially advantageous for producing improved microorganisms used for the biocatalytic production of chemicals and vitamins where numerous catalytic events are taking place either concurrently or sequentially within the host microorganism. In such complex biocatalytic systems, it is often difficult to identify the specific molecular events causing low yields, host toxicity or catalytic failures and therefore difficult if not impossible to understand which specific genetic events to alter in order to correct the deficiencies. The methods of the present invention provide the advantage of allowing the microorganism to make the required changes in response to selective pressure.

Additionally, the methods of the present invention provide an advantage for obtaining microorganisms comprising desired phenotypic traits associated with multiple genes, such as the ability of a microorganism to grow at elevated temperatures. The use of the mutator gene provides a means for producing genetic diversity and the simultaneous growth under conditions of selective pressure allows the microorganism to identify the specific genetic changes required for survival. The use of mutD gene mutations allows for very large diversity to be provided to the microorganism from which to select for the specific genetic changes that provide a growth advantage. Therefore, the methods disclosed herein avoid the limited diversity that is often produced with art methods that begin the directed evolution process with defined sets of genes. Furthermore, the methods disclosed herein eliminate additional screening steps often associated with art methods for producing genetic diversity. A further advantage of the present invention is that the methods can be applied to microorganisms which have not been sequenced and for which there may be limited information upon which to design genetic changes.

In illustrative embodiments disclosed herein, a mutated mutD gene residing on a plasmid was introduced via recombinant techniques into E.coli or E.blatte. The E.coli or E.blatte cell was then cultured under conditions suitable for growth for a time sufficient for at least 20 doublings and up to at least about 2000 doublings under conditions of selective pressure. In one example, E.coli was grown under conditions of increased temperature or in the presence of DMF and in another E.blattae was growth in the presence of solvent, such as DMF or 1,3 propanediol. As a result, E.coli was evolved into a microorganism capable of growing at temperatures up to about 48° C. or in the presence of 80 g/l DMF. E.coli evolved to grow at elevated temperatures also became auxotrophic for three amino acids, Cys/Met, Asp/Asn and Pro. E.blattae was evolved into a microorganism capable of growing anaerobically in the presence of at least 105 g/l 1,3-propanediol and which comprised genetic changes in at least one catalytic activity associated with 1,3 propanediol production, 1,3-propanediol dehydrogenase, shown in FIG. 3.

The use of a plasmid comprising a mutator gene, ie, a mutator plasmid, can be used to control the mutation rate of a microorganism. As described under Section II below, plasmid constructs can be designed which provide reduced levels of expression of a mutator gene thereby providing a means for altering the ratio of naturally occurring DNA repair genes vs mutator genes. This provides a means for combining the advantage of mutD mutations (which results in random mutagenesis) with the advantages of the other known mutators (lower mutation frequency which leads to a lower burden on the cells). Additionally, plasmid constructs can be designed that allow for curing the evolved microorganism of the mutator gene, such as the use of a temperature sensitive origin, thereby allowing for a means for turning the mutation events off and on in the microorganism. For a gram positive microorganism, such as B.subtilis where the entire genome has been sequenced, the present invention could encompass the steps of deleting or mutating a DNA repair gene, evolving the Bacillus, and restoring the naturally occurring DNA repair system through recombination events. As disclosed herein, several members of Escherichia, such as E.coli and E.blatte have been subjected to the directed evolution methods. Illustrative examples of evolved E.coli and E.blattae have been deposited with the ATCC and have accession numbers, PTA-91 and PTA-92, respectively.

The methods of the present invention provide a means to accomplish longterm evolution of microorganisms. An E.coli strain comprising a plasmid comprising a mutD mutation was grown for>1000 doublings without a reduction in mutation rate. The present invention also provides a means for reducing the functional genome of an organism. A microorganism can be grown for many thousands of generations, such that only the genes which are essential would remain functional. Most of the other genes would carry random and inactivating mutations.

The present invention also provides a means for making non-pathogenic organisms. A pathogenic strain can be evolved into a mutator strain by introduction of a mutator gene and grown for extended periods of time. As a result many of the genes that are involved in pathogenicity would become inactivated and the strain would be safe to use.

The present invention also provides a means to streamline the metabolism of an organism. A strain which has an improved yield on nutrients or a reduced metabolic rate (maintenance metabolism) can be produced by methods disclosed herein. Such strains would be useful production strains for chemicals as well as enzymes. The present invention provides a means for making microorganisms mutator strains by introducing a mutator gene, thereby protecting the microorganism's naturally occurring DNA repair genes from becoming mutator genes in response to selective pressure. That is, the introduction of the mutator plasmid into a microorganism whether via a plasmid or into the genome, protects the cells from developing a mutator phenotype in response to selective pressure.

II. Mutator genes and frequency of mutations

Mutator genes of the present invention include but are not limited to, mutations of the DNA repair genes mutD, mutT, mutY, mutM, mutH, mutL, mutS or mutU or their homologues in other microorganisms. A description of the DNA repair genes are disclosed in Miller, supra; mutD is disclosed in Maki et al., 1983, Proc. Natl. Acad. Sci., U.S.A. 80, 7137–7141 (GenBank accession number K00985.1 GI: 147678 and FIG. 1); B. subtilis mutS and mutL are disclosed in Ginetti et al., 1996, Microbiology, Aug, 142 (Pt 8): 2021–9; Streptococcus pneumoniae hex B repair gene, mutL of Salmonella typhimurium and PMS1 of Saccharomyces cerevisiae are disclosed in Prudhomme et al., 1989, J. Bacteriology, Oct; 171 (10): 5332–8; Streptococcus pneumoniae hexA and mutS of *Salmonella typhimurium* and *E.coli* are disclosed in Priebe et al., *J. Bacteriol*, 1988, Jan; 170(1): 190–6 and Prudhomme et al., 1991, *J. Bacteriol*. Nov; 173(22): 7196–203; human mutS homologue, hMSH2, and human MutL homologue, hMLH1, are disclosed in Macdonald et al., 1998, *Heptology*, Jul 28(1):90–7; the mut-1 of Neurospora is disclosed in Dillon et al.,1994, *Genetics*. Sep 138(1):61–74 and yeast homologues of mutL and mutS are disclosed in WO 97/15657. The methods of the present invention comprises the use of at least one of the mutant DNA repair genes and may involve the use of more than one. It is preferred that a mutator gene be dominant to the wild type gene of the microorganism such that mutations are introduced into the genome of the microorganism. In a preferred embodiment, the mutator gene is a mutation of the mutD gene. The nucleic acid and amino acid sequence for mutD is shown in FIG. 1. One particular mutD mutation, mutD5, is disclosed in Takano, K., et al., (1986, *Mol Gen Genet* 205, 9–13, Structure and function of dnaQ and mutD mutators of *Escherichia coli*). Strain CSH116 was obtained as disclosed in Miller, J. H. (1992, A Short Course in Bacterial Genetics). This strain is reported to carry the mutD5 allele. The mutD gene in this strain was found to be very different from the published mutD5. The mutD gene from strain CSH116 is designated herein as mutD5'. Table I gives the mutations found in mutD5 and mutD5'. Further mutations in mutD which result in increased levels of mutation frequency were identified recently in Taft-Benz, S. A. et al., (1998, *Nucl. Acids Res.* 26, 4005–4011, Mutational analysis of the 3'–5' proofreading exonuclease of *Escherichia coli* DNA polymerase III). Table I describes various mutD mutations useful in the present invention. Table II describes various promoters used with the mutD mutations and Table III describes mutator plasmids and the range of available mutation frequencies in *E.coli*.

TABLE I mutations in the coding region of mutD

| | MutD | | | Clone | | |
|---|---|---|---|---|---|---|
| # nucleotide | #amino acid | nucleotide | amino acid | nucleotide | amino acid | |
| 44 | 15 | C | Thr | T | Ile | mutD5' |
| 218 | 73 | T | Leu | G | Trp | mutD5 |
| 369 | 123 | T | Thr | C | Thr | mutD5' |
| 418 | 138 | C | Pro | T | Pro | mutD5' |
| 451 | 151 | T | Ala | C | Ala | mutD5' |
| 484 | 161 | G | Leu | A | Arg | mutD5' |
| 491 | 164 | C | Ala | T | Val | mutD5 |
| 661 | 220 | A | Glu | C | Asp | mutD5' |
| 665 | 222 | A | Ile | C | Leu | mutD5' |
| 673 | 225 | T | Ala | A | Ala | mutD5' |
| 688 | 228 | C | Leu | T | Leu | mutD5' |
| 706 | 236 | A | Lys | G | Lys | mutD5' |
| 715 | 239 | T | Ser | C | Ser | mutD5' |
| 727 | 243 | A | Arg | G | Arg | mutD5' |

TABLE II mutD Mutations

| Name | Mutations | |
|---|---|---|
| wild type | ATGACCGCTATG . . . | SEQ ID: 5 |
| pOS100 | TTGA-CGCTTTG . . . | SEQ ID: 6 |
| pOS101 | GTGACCGCTGTG . . . | SEQ ID: 7 |
| pOS102 | GTG-CCGCTGTG . . . | SEQ ID: 8 |
| pOS104 | TTGACCGCTTTG . . . | SEQ ID: 9 |
| pOS105 | GTGACCGCTGTGAGCACTT(G)CAATTACACGCCAGATCGTTCTCGATACCGAAAT(C) . . . | SEQ ID: 10 |
| pOS106 | GTGACCGCT-TG . . . | SEQ ID: 11 |

TABLE III

Mutator (mutD5) and control (mutD) plasmids and the range of available mutation frequencies in *E. coli*.

| # | plasmid | genotype | ori | ab resistance | size (kb) | mut. Frequency (average) | mutator rate (relative) |
|---|---|---|---|---|---|---|---|
| 1 | pMutD5-61 | mutD5' | pSc | kan | 5.97 | $6.4 \times 10^{-5}$ | ~1000-fold |
| 2 | pMutD71-Ts | mutD | pSc | kan | 5.97 | $2.5 \times 10^{-8}$ | wild type |
| 3 | pBRmutD68 | mutD5' | pBR322 | kan, bla | 6.16 | $1.1 \times 10^{-4}$ (AL data) | ~10000-fold |
| 4 pBRmutD727 Modified | | mutD | pBR322 | kan, bla | 6.16 | nd | wild type |
| 5 | pOS100 | mutD5' | pBR322 | kan, bla | 6.16 | $2 \times 10^{-5}$ | ~800-fold |
| 6 | pOS101 | mutD5' | pBR322 | kan, bla | 6.16 | $3.8 \times 10^{-6}$ | ~152-fold |
| 7 | pOS102 | mutD5' | pBR322 | kan, bla | 6.16 | $1.1 \times 10^{-6}$ | ~44-fold |
| 8 | pOS104 | mutD5' | pSc | kan | 5.97 | $4.35 \times 10^{-7}$ | ~17-fold |
| 9 5 | pOS10 mutD5' | pSc | kan | 5.97 | $1.1 \times 10^{-6}$ | ~44-fold | |
| 10 | pOS106 | mutD5' | pSc | kan | 5.97 | $5 \times 10^{-6}$ | ~200-fold |

MutD mutations can introduce all types of base pair changes including frame shifts (Miller, supra). MutD5 has a reported relative mutation frequency of 1000–10000 fold in rich medium, ie, $5 \times 10^{-6}$ to $5 \times 10^{-7}$ mutations per doubling per base pair (Denegen et al., 1974,J. Bacteriol. 117, 477–478). Considering that the *E.coli* genome has $4.6 \times 10^6$ bp, then a mutD5 gene will generate 2.3 to 23 mutations per doubling per genome. In a preferred embodiment of the present invention, mutator plasmids have been generated which allow for reduced expression levels of the mutated mutD repair gene such that the mutation rate relative to wild type is reduced. As illustrated in Table II, the MutD gene has 2 closely located ATG start codons with 6 nucleotides between them. The first ATG is considered to be putative. Both ATG codons were replaced with GTG or TTG codons for reducing mutD5' expression levels. The space between the 2 ATG codons up to 5 nucleotides was truncated. The plasmids comprising these mutator genes provide lower mutation rates when introduced in *E.coli* in comparison to MutD5' plasmids.

As a result, the microorganism comprising the plasmid comprising the mutated mutD gene expressed normal levels of the functional epsilon subunit coded by naturally occurring mutD and low amounts of the non-functional epsilon subunit coded by the mutated mutD5'. Both subunits compete for polymerase III. Consequently, the microorganism will most of the time have functional proof-reading but to a certain fraction of time the cell will copy its DNA without proof-reading, due to the presence of the mutD mutations. Thus, the frequency of mutagenesis of a microorganism can be altered by adjusting the expression of the mutator gene or by altering the ratio of a naturally occurring DNA repair gene to the corresponding mutated DNA repair gene. The mutations caused by these plasmid introduced mutator genes should still be as random as mutations caused by a chromosomal copy of mutD5. Data generated in Example III indicate that mutation rates of 5–1000 times over wild type are preferred for most applications. Other means of controlling the mutation frequency include having two copies of mutD on the plasmid or integrated into the microrganism genome and/or using a transmissible heat sensitive plasmid which could be used to temporarily transform cells into mutators and then restore them to wild type rates. Yet another way to adjust the mutation frequency is to identify mutD mutations which result in moderate mutation frequency due to reduced proof reading. Such mutants have been recently identified but it is not known if these mutations preferentially result in a few types of specific mutations, Taft-Benz et al., 1998, Nucl. Acids. Res. 26:4005–4011. Mutation rates are determined using rifampicin or streptomycin as disclosed in Horiuchi, et al., 1978, Mol. Gen. Genet. 163:227–283.

Mutation rates and a description of the molecular fingerprint of a microorganism produced by the methods disclosed herein and claimed are also exemplified by virtue of the microorganism deposits made with the ATCC under the terms of the Budapest treaty.

III. Construction of mutator genes and mutator plasmids

Construction of plasmids comprising mutator genes and transformations of microorganisms can be performed by means deemed to be routine to the skilled artisan. In one embodiment illustrated herein, nucleic acid encoding a mutator gene is introduced into a microorganism on a replicating plasmid, ie, a mutator plasmid, which is cured or otherwise eliminated from the microorganism after evolution. In another embodiment disclosed herein, nucleic acid encoding a mutator gene is introduced into a microorganism's genome in addition to or as a replacement of a naturally occurring DNA repair gene.

Nucleic acid encoding a mutator gene can be isolated from a naturally occurring source or chemically synthesized as can nucleic acid encoding a protein or enzyme. Sources for obtaining nucleic acid encoding DNA repair genes mutD, mutT, mutY, mutM, mutH, mutL, mutS or mutU is provided in Section II. FIG. 1 provides the nucleic acid and amino acid sequence for mutD and Table I and III provide preferred mutations for mutD and the mutation rates obtained for each construct. Once nucleic acid encoding a mutator gene is obtained, plasmids or other expression vectors comprising the mutator gene may be constructed using techniques well known in the art. Molecular biology techniques are disclosed in Sambrook et al., *Molecular Biology Cloning: A Laboratory Manual*, Second Edition (1989) Cold Spring Harbor Laboratory Press, Cold Spring Harbor, N.Y. (1989) and Brown, T. *Current Protocols in Molecular Biology*, Supplements 21, 24, 26 and 29. Nucleic acid encoding a mutator gene is obtained and transformed into a host cell using appropriate vectors. A variety of vectors and transformation and expression cassettes suitable for the cloning, transformation and expression in bacteria are known by those of skill in the art.

Typically, the plasmid vector contains sequences directing transcription and translation of the nucleic acid, a selectable marker, and sequences allowing autonomous replication or chromosomal integration. Suitable vectors comprise a region 5' of the gene which harbors transcriptional initiation controls and a region 3' of the DNA fragment which controls transcriptional termination. These control regions may be derived from genes homologous or heterologous to the host as long as the control region selected is able to function in the host cell.

Initiation control regions or promoters, which are useful to drive expression of the mutator gene. Virtually any promoter capable of driving expression is suitable for the present invention. Once suitable cassettes are constructed they are used to transform the host cell. General transformation procedures are taught in Current Protocols In Molecular Biology (Vol. 1, edited by Ausubel et al., John Wiley & Sons, Inc., 1987, Chapter 9) and include calcium phosphate methods, transformation using PEG, electroporation and protoplast transformation.

After subjecting a microorganism to directed evolution using a mutator plasmid, the microorganism is cured of the mutator plasmid in order to restore the microorganism to wild-type mutation rates. Methods for curing a microorganism of a resident plasmid comprising a mutator gene include transformation of the microorganism comprising a mutator plasmid with an incompatible plasmid; electroporation techniques as described in Heery et al., 1989, *Nucl. Acids. Res.*, 17: 10131; growth with acridine orange or ethidium bromide in the medium (Jeffrey Miller, 1972, in Curing of Episomes from *E.Coli* strains with Acridine Orange from Experiments in Molecular Genetics, Cold Spring Harbor Laboratories, pg. 140). In this method, acridine orange is added to 5 ml cultures of an Enterobacteriaceae strain at 125 μg/ml and allowed to grow overnight at 37° C. The following day, the cultures are plated out and individual colonies are used to prepare plasmid nucleic acid. The nucleic acid is analysed by means known to those of skill in the art to determine the presence or absence of the plasmid. For microorganisms comprising a mutator gene in their genome, techniques known to those of skill in the art can be used to restore the microorganism back to wild-type mutation rates, such as excising the mutator gene or replacing the mutator gene with the naturally occurring DNA repair gene through homologous recombination techniques.

IV. Culture conditions and selective pressure

Once a microorganism has been exposed to a mutator gene, it is cultured under conditions of desired selective pressure, such as elevated temperature, pH, salt or in the presence of a solvent, such as, for example, DMF or 1,3 propanediol. Examples of other solvents include alcohols, diols, hydrocarbon, mineral oil, mineral oil derived products, halogenated compounds and aromatic compounds.

As the skilled artisan will appreciate, growth conditions are strain dependent. General growth conditions are disclosed in Truesdell et al., (1991, *Journal of Bacteriology*, 173: 6651–6656) and Sonoyama et al. (1982, *Applied and Environmental Microbiology*, Vol. 43, p.1064–1069). Culture media may be supplemented when selectable markers are present such as antibiotic resistance genes, including but not limited to tetracycline, ampicillin or chloramphenicol.

For the methods of the present invention, cultures may be grown aerobically or anaerobically in either liquid medium or solid medium, depending upon the microorganism and the type of selection. If cultures are grown in liquid medium, it is preferred to undergo a number of rounds of replication (20 or more) in order to allow the survivors of the selection to grow over the wild-type. If cultures are grown in solid medium, such as on an agar plate, it is preferred to have a number of repetitive platings in order to pick the survivors directly and to apply higher selection pressure in each round and to amplify the population that is able to grow under the specific conditions of selection.

The manner and method of carrying out the present invention may be more fully understood by those of skill in the art by reference to the following examples, which examples are not intended in any manner to limit the scope of the present invention or of the claims directed thereto.

EXAMPLES

Example 1

Construction of mutD and mutD5' plasmids and testing in 3 bacterial strains.

The following example illustrates the construction of plasmids comprising the mutator gene, mutD5'.

mutD and mutD5' genes were amplified by PCR using mutd1 (5'-CGCCTCCAGCGCGACAATAGCGGCCATC-3') SEQ ID NO: 12 and mutd2(5'-CCGACTGAACTACCGCTCCGCGTTGTG-3') SEQ ID NO: 13 primers from genomic DNA of *E. coli* and *E. coli* CSH116 (Miller 1992), respectively. The PCR products were cloned into pCR-Blunt vector (Invitrogen, Carlsbad, Calif.). Plasmids from clones with the correct orientation were isolated and digested with SmaI-HindIII restriction enzymes. The overhang ends were filled using T4 polymerase and cloned into pMAK705 plasmid digested with SmaI-PvuII. The ligation products were transformed into JM101 competent cells. The resulted plasmids had the temperature-sensitive origin of replication, carried kanamycin resistance marker and were named pMutD-71 (control plasmid, wild type genotype) and pMutD5-61 (mutator plasmid).

The plasmids were successfully tested in *E. coli* MM294 (F⁻endA1 hsdR17 ($r_k^- m_k^+$)supE44 thi-1 relA1) and *E. blattae* ATCC accession number 33429 for evolution of solvent tolerance. All evolution experiments were performed in LB medium. Mutation rates were determined by plating aliquots of cell suspensions on LB plates containing 100 ug/ml rifampicin or streptomycin. The mutation frequency was calculated by dividing the number of resistant cells by the total number of plated cells.

Example 2

Evolution of solvent tolerance.

The following example illustrates the evolution of solvent tolerant microorganisms using the mutator plasmids constructed as in Example 1.

In order to make evolution experiments quantitative, LB agar plates supplemented with 50, 60, 70, 80 and 90 g/l DMF and 25 ug/ml kanamycin were used. The size of every evolving population was limited to $10^6$ cells. After each plating, the number of raised colonies was counted and 10 were selected for the next plating. Cells from selected colonies were mixed together and aliquots containing $10^6$ cells were plated on fresh plates containing the same and higher concentrations of DMF. After 2 consequent platings the cells were cured of the plasmids by growth at elevated temperatures. *E. blattae* 33429 and *E. coli* MM294 were cured at 41° C. and 43° C., respectively. Three to four subculturings at indicated temperatures were sufficient for 87–100% curing. Individual cured clones were selected by parallel growth of clones in selective and non-selective medium. The curing was also confirmed by plasmid purification from selected clones and gel analysis.

The cured strains were tested for growth with the same DMF concentrations as their plasmid containing parents. The experiment demonstrates (1) the advantage of strains harboring mutator plasmids over strains carrying control plasmids and (2) the preservation of evolved features in strains cured from mutator plasmids.

The results of the short-term evolution are summarized in Table IV. In the process of 2 platings we obtained *E. coli* colonies, which were able to grow on plates containing 20 g/l higher concentration of DMF than control clones. Analysis of *E. coli* MM294 harboring control and mutator plasmids revealed that the mutation frequency of cells carrying control plasmids was more then 3 orders of magnitude lower in comparison with cells containing mutator pMutD5-61. Our results showed that hypermutation was very beneficial for cell survival at elevated DMF concentrations (Table V). *E. blattae* 33429 appeared to be more sensitive to DMF. Population of $10^6$ cells raised 968 colonies during 2 plating. When 10 bigger colonies were mixed and a new aliquots of $10^6$ cells were plated on DMF plates supplemented with 70 g/l DMF, more than 1000 tiny colonies grew on the plates. However, these small colonies were not viable after transfer on fresh 70 g/l DMF plates. The mutation frequency of *E. blattae* 33429(pMutD5-61) dropped from $4.55 \times 10^{-6}$ to $1.1 \times 10^{-7}$ after second plating on plates containing 60 g/l DMF (Table V). Plasmid MutD5-61 initially provided lower mutation frequency in *E. blattae* in comparison with *E. coli*. The *E. blatte* strain distinctly reduced mutability after cultivation in the presence of DMF. Although *E. coli* and *E. blattae* strains belong to the family Enterobacteriaceae, the behavior of *E. coli* mutD5 gene product could be somewhat different in *E. blattae* cell environment. Nevertheless, the benefits of pMutD5 for survival of *E. blattae* on 60 g/l DMF plates were obvious. Control cells carrying pMutD-71 couldn't grow in the presence of DMF above 50 g/l.

Contrary to *E. blattae* 33429(pMutD5-61), we did not observed significant adjustments of mutability in *E. coli* strains. The mutation frequency stayed within the same range at the end of evolution experiment. (Table V).

Single colonies of evolved cultures were used for curing experiments. The curing efficiency was 87–100% with *E. blattae* 33429 and *E. coli* MM294. The mutation frequencies of cured clones were similar to wild type control frequencies, and cured clones preserved their ability to grow at elevated DMF concentration. *E. blattae* 33429 cured clones grew with 60 g/l DMF and E. coli MM294 grew with 80 g/l DMF. Initial tolerance of MM294 and E.blattae 33429 was 60 g/l and 50 g/l DMF respectively. The evolved strains increased their tolerance by 20 g/l and 10 g/l DMF, respectively. Therefore, sensitivity to DMF is strain dependent.

The advantage of mutator plasmids for evolution in liquid culture was tested as well. Within 4 days of solvent tolerance evolution in liquid medium supplemented with DMF or ethanol, E. blattae 33429(pMutD5-61) demonstrated growth at higher concentrations of both solvents in comparison with control cultures.

Mutator plasmids can be applied for evolution of bacterial tolerance to different solvents, various environmental stress and potentially toxic specialty chemicals of industrial biotechnology. One advantage of the directed evolution methods disclosed herein is that the evolution of microorganisms carrying mutator plasmids can be stopped at any time. Mutator plasmids can be cured from evolving strains, and therefore, evolved desired features of the whole strain can be preserved.

TABLE IV

Evolution of solvent tolerance. Colony formation by resistant clones on LB plates supplemented with various DMF concentrations.

| Strain | Genotype | DMF (g/l) | Plating 1 Number of colonies* | Plating 2 Number of colonies* |
|---|---|---|---|---|
| MM294 (pMutD5-61) | Mutator | 60 g/l | low density lawn | high density lawn |
| MM294 (pMutD5-61) | Mutator | 70 g/l | 11 | 824 |
| MM294 (pMutD5-61) | Mutator | 80 g/l | 0 | 4 |
| MM294 (pMutD-71) | Wild type | 60 g/l | 17 | low density lawn |
| MM294 (pMutD-71) | Wild type | 70 g/l | 0 | 0 |
| EB33429 (pMutD5-61) | Mutator | 50 g/l | low density lawn | high density lawn |
| EB33429 (pMutD5-61) | Mutator | 60 g/l | 0 | 968 |
| EB33429 (pMutD-71) | Wild type | 50 g/l | 793 | high density lawn |
| EB33429 (pMutD-71) | Wild type | 60 g/l | 0 | 0 |

*The number of colonies represents survivors from $10^6$ cells plated on LB-DMF plates.

TABLE V

Mutation frequencies of bacteria harboring mutator and control plasmids.

| Strain | Mutation rate before the evolution | Mutation rate DMF (g/l)* | after the evolution |
|---|---|---|---|
| MM294 (pMutD5-61) | $9.2 \pm 6.5 \times 10^{-5}$ | 80 g/l | $4.7 \pm 4 \times 10^{-5}$ |
| MM294 (pMutD-71) | $4.15 \pm 3.4 \times 10^{-8}$ | 60 g/l | $2.9 \pm 2.4 \times 10^{-8}$ |
| EB33429 (pMutD5-61) | $4.55 \pm 3.7 \times 10^{-6}$ | 60 g/l | $1.13 \pm 0.9 \times 10^{-7}$ |
| EB33429 (pMutD-71) | $2.6 \pm 2.1 \times 10^{-8}$ | 50 g/l | $4.7 \pm 3.8 \times 10^{-8}$ |

*Single colonies from LB-DMF plates were grown in LB medium to OD $A_{620}$ = 0.8–1.2. and plated on LB-Rifampicin or Streptomycin plates at 30° C. The experiments were done in triplicates.

Example 3

Evolution of high temperature strains.

Example 3 illustrates high temperature evolution under conditions of continuous fermentation in the mode of turbidostat which allows for fermentation wherein the cell density is stabilized. Two independent experiments were run with the strains: A: W1485 (ATCC12435) (=non mutator); B: W1485/pBRmutD68 (same strain but comprises mutator plasmid). Both strains were gown in continuous culture in a turbidostat in LB medium for about 1800 doublings. The temperature was controlled by a computer based on the measured growth rate to maintain a doubling time of about 1 h. Whenever the culture grew faster the temperature was raised and vice versa. The time course of both cultures is shown in FIG. 4. Initially, the culture started from W1485/pBRmutD68 evolved faster than the culture started from W1485. This indicates the advantage of the mutator plasmid. However, After about 400 doublings W1485 reached the higher temperature. We also measured the mutation rate of samples taken from both evolution experiments. Table 6 shows that the starting clones differed in their mutation frequencies by a factor of 3000. However, during the evolution experiments the mutation frequencies converged to within a factor of 2. The experiment illustrates that the rate of temperature evolution slows down over the course of the experiment. It can be expected that in a wild type strain there are a small number of genes which initially limit growth at elevated temperature. Favorable mutations in these genes will lead to relatively large gains in fitness. However, with increasing temperature more and more genes can be expected to limit growth and the pace of evolution slows down. If individual mutations result in only very small growth benefits to their carrier then the populations have to be grown for a significant number of doublings to enrich the clones carrying these mutations from the population. As a consequence the optimum mutation rate for evolution will decrease during the process of evolution. For Table VI, mutation rates were determined using rifampicin as given in Miller (1992, supra).

TABLE VI

Mutation rates of strains and populations used for temperature evolution

| Strain/population | doublings | temperature ° C. | mutation rate |
|---|---|---|---|
| W1485/pBRmutD611 | 0 | 45 | 3142.9 |
| AL018 | 210 | 47.22 | 3428.6 |
| AL019 | 376 | 47.50 | 2028.6 |
| AL038 | 1811 | 48.21 | 1142.9 |
| W1485 | 0 | 45 | 1.0 |
| AL017 | 231 | 47.10 | 0.9 |
| AL035 | 543 | 47.91 | 134.3 |
| AL040 | 1385 | 48.57 | 514.3 |

Example 4

Directed evolution of E. blattae and selection in the presence of a solvent, 1,3-propanediol.

E. Blattae ATCC accession number 33429 was transformed with plasmid pMutD68 (see Table III) and cultured in media containing 1, 5, 10, 20, and 30 g/l 1,3 propanediol (cultures are designated as GEBxxx where "xxx" indicates the number of transfers into fresh media). All directed evolution experiments were carried out under anaerobic conditions in defined minimal medium with glycerol as a sole carbon source. E. blattae doesn't require vitamin $B_{12}$ for growth, nevertheless, initial experiments were performed in 2 conditions (1) with $B_{12}$, and (2) without $B_{12}$ in the growth medium.

Within 18–22 h GEB001 reached maximum 1030–1060 mOD ($A_{650}$) at all concentrations of 1,3 propanediol. Therefore, 30 g/l 1,3-PD was not inhibitory for GEB001 growth. Growth rates of GEB in the presence of 50 g/l were ~½ of growth rates in the presence of 30 g/l 1,3-PD (590 mOD: 1030 mOD in 22 h). The threshold of tolerance to 1,3-PD was found between 70 to 80 g/l. After 10 transfers, GEB010 was able to grow in the presence of 80 g/l 1,3-PD to 350 mOD within 78 h. However, these cells failed to grow at 80 g/l 1,3-PD concentration after next transfer.

E.blatte is known in the art to carry the enzymatic pathway for the production of 1,3 propanediol (Roth, et al., 1986, Annu. Rev. Microbiol. 50:137–181). In order to determine if E.blatte can make 1,3-propanediol in addition to the concentrations of 1,3 propanediol added to the medium, GEB011 was grown in medium supplemented with 2-$^{13}$C glycerol and 70 g/l 1,3-PD. The supernatant was then analyzed by NMR ($^{13}$C) and the results indicated the formation of ~2.6 g/l $^{13}$C 1,3-PD. Therefore, GEB cells can make 1,3 propanediol in the presence of 1,3-PD.

The evolution of 1,3-propanediol resistance was faster in the presence of B12. After 2 months of evolution GEB025 (+B12) was able to grow with 95–100 g/l 1,3-propanediol. After 3 months of anaerobic growth under selection in the presence of 1,3-propanediol, GEB028 (–B12) could grow in medium supplemented with 110 g/l 1,3-propanediol. Analysis of aerobic growth of GEB031 on LB plates supplemented with 85, 95, 105 and 115 g/l 1.3-propanediol showed that cells produce much bigger colonies in the presence of 85 g/l in comparison with 105 g/l. No growth was observed at 115 g/l 1,3 propanediol. The results indicate that after 3 months of applying directed evolutions techniques described herein to E.blattae, the tolerance to 1,3 propanediol was increased from 75 g/l to at least 105 g/l under aerobic conditions. The plasmid was cured from the GEB031 strain by growing at 41.5 degrees. An illustrative clone, GEB031-4 was deposited with the ATCC and has accession number PTA-92.

Example 5
Genetic changes in evolved E.blattae.

1,3-propanediol dehydrogenase (PDD) was compared between wild type E. blattae and the evolved strain GEB031. The PDD from the evolved strain had a higher Km for 1,3- propanediol.

Materials and Methods

Strains—Wild type ATCC 33429, E.blattae comprising the mutant PDD as described in Example 4 and having ATCC accession number PTA-92.

Growth—Cells were grown in a complex medium at 30 C 500 ml in a 2800 ml fernbach with shaking at 225 rpm for 20 hr. The medium consists of KH2PO4, 5.4 g/L; (NH4)2SO4, 1.2 g/L; MgSO47H2O, 0.4 g/L; yeast extract, 2.0 g/L; tryptone, 2.0 g/L; and glycerol, 9.2 g/L in tap water. The pH was adjusted to 7.1 with KOH before autoclaving (Honda, et al., 1980, J. Bacteriol, 143:1458–1465).

Extract prep—Cells were harvested by centrifugation with care to avoid anaerobic conditions. Pellets were resuspended in 100 mM Tricine pH 8.2 containing 50 mM KCl and 1 mM DTT. Cells were disrupted by passage through a French pressure cell. Crude extracts were clarified by centrifugation at 20 Kxg for 20 min followed by 100 Kxg for 1 hr to yield the high speed supernatant (HSS) fraction.

Assays—the assay for PDD was performed as described by Johnson, E. A. et al., 1987, J. Bacteriol. 169:2050–2054.

Partial purification of PDD—HSS was separated on a 16x100 Poros 20 HQ column. The buffers were A, 50 mM HEPES, pH 7.4 containing 100 uM MnCl and B, A buffer containing 500 mM KCl. The column was loaded and developed at 10 ml/min. The gradient was 10 CV wash, a linear gradient to 70% B in 10 CV, and 1 CV to 100% B. The activity was detected in the very early fractions of the gradient. Pooled column fractions of the 33429 strain were used as collected for assays after the addition of additional of DTT to 1 mM. The active fractions from strain GEB031 were pooled and concentrated on a PM30 membrane and used as concentrated after the addition of additional 1 mM DTT.

| Strain | GD (U/mg) | PDD (U/mg) | Ratio GD/PDD |
|--------|-----------|------------|--------------|
| 33429  | 0.64      | 0.22       | 2.9          |
| GEB031 | 0.79      | 0.08       | 9.9          |

PDD Kinetics—The results are shown below.

| Strain | Km (mM Propanediol) | Km (uM AND) |
|--------|---------------------|-------------|
| 33429  | 28                  | 57          |

Example 6
Cloning and sequencing the 1,3-propanediol dehydrogenase genes (dhaT) from E blattae.

The dhaT genes were amplified by PCR from genomic DNA from E. blattae as template DNA using synthetic primers (primer 1 and primer 2) based on the K. pneumoniae dhaT sequence and incorporating an XbaI site at the 5' end and a BamHI site at the 3' end. The product was subcloned into pCR-Blunt II-TOPO (Invitrogen). The cloning dhaT were then sequenced with standard techniques. The results of the DNA sequencing are given in SEQ ID NO:3 and SEQ ID NO:4.

Primer 1 5' TCTGATACGGGATCCTCAGAATGCCTG-GCGGAAAAT3' SEQ ID NO:14

Primer 2 5' GCGCCGTCTAGMTTATGAGCTATCG-TATGTTTGATTATCTG3' SEQ ID NO:15

As will be readily understood by the skilled artisan, nucleic acid sequence generated via PCR methods may comprise inadvertent errors. The present invention also encompasses nucleic acid encoding PDD obtainable from E.blattae having ATCC accession number PTA-92.

Example 7
Comparison of wild-type E.blattae (ATCC accession number 33429) and the evolved strain GEB031-4 (ATCC accession number PTA-92).

This example shows that E.blattae subjected to the methods of the present invention and having ATCC accession number PTA-92 can completely consume 800 mM glycerol during anaerobic fermentation and does not accumulate 3-hydroxy-propionaldehyde (3HPA) and does not lose viability. In contrast, the wild-type E.blattae accumulates 50 mM 3 HPA and becomes non viable after consuming only 350 mM glycerol.

The wild-type E.blattae and the evolved E.blattae were subjected to fermentation in the following medium: 75 g glycerol, 5 g $K_2HPO_4 \cdot 3H_2O$, 3 g $KH_2PO_4$, 2 g $(NH_4)_2SO_4$, 0.4 g $MgSO_4 \cdot 7H_2O$, 0.2 g $CaCl_2 \cdot 2H_2O$, 4 mg $CoCl_2 \cdot 2H_2O$, 2 g yeast extract, and 1 g peptone per liter water. The pH was maintained with 20% NaOH. Both fermentations were run at 30° C. with a $N_2$ sparge and were inoculated with a stationary grown overnight preculture.

The wild-type *E.blattae* accumulated 3HPA and stopped growing and metabolizing glycerol. The accumulation of 3HPA was high and reached 50 mM. The cell density did not change with the culture age, but viability of the cells did. Plate counts demonstrated that accumulation of 3HPA was toxic. In contrast, the evolved strain did not accumulate more than about 6 mM 3HPA and did not lose viability with culture age. After the culture had consumed all of the glycerol more was added and the culture continued converting glycerol to 1,3-propanediol. See FIGS. 5 and 6.

All references cited herein, including patents, patent applications, sequences and publications are hereby incorporated in their entirety by reference.

We claim:

1. A method for preparing an evolved microorganism comprising the steps of:
   a. culturing a microorganism comprising at least one heterologous mutator gene for at least 20 doublings under conditions suitable for selection of an evolved microorganism, wherein said heterologous mutator gene generates a mutation rate of at least 5–100,000 fold relative to wild type, and
   b. restoring said evolved microorganism to a wild type mutation rate.

2. The method of claim 1 wherein said microorganism further comprises at least one introduced nucleic acid encoding a heterologous protein.

3. The method of claim 2 wherein said heterologous protein(s) is/are selected from the group consisting of hormones, enzymes and growth factors.

4. The method of claim 1 wherein said microorganism is cultured for between about 20 to about 100 doublings.

5. The method of claim 1 wherein said microorganism is cultured for between about 100 to about 500 doublings.

6. The method of claim 1 wherein said microorganism is cultured for between about 500 to about 2000 doublings.

7. The method of claim 1 wherein said microorganism is cultured for greater than 2000 doublings.

8. The method of claim 1 wherein said evolved microorganism comprises from about 3 to about 1000 selected mutations.

9. The method of claim 1 wherein said evolved microorganism further comprises from about 20 to about 100,000 neutral mutations.

10. The method of claim 1 wherein said evolved microorganism comprises about 3 to about 1000 selected mutations in about 3 to about 500 genes.

11. The method of claim 10 wherein said mutations are non-specific.

12. The method of claim 10 wherein said mutations are specific.

13. The method of claim 1 wherein said mutator gene generates a mutation rate of at least about 5 fold to about 10,000 fold relative to wild type.

14. The method of claim 1 wherein said mutator gene generates a mutation rate of at least about 5 fold to about 1000 fold.

15. The method of claim 1 wherein said mutator gene generates a mutation rate of about 5 fold to about 100 fold over wild type.

16. The method of claim 1 wherein said microorganism comprises a plasmid comprising the heterologous mutator gene and said step of restoring said evolved microorganism to a wild type mutation rate comprises curing the evolved microorganism of said plasmid.

17. The method of claim 16 wherein said plasmid comprises a temperature sensitive origin of replication.

18. The method of claim 1 wherein said conditions suitable for selection comprise culturing said microorganism in the presence of at least one organic solvent.

19. The method of claim 18 wherein said organic solvent is selected from the group consisting of alcohols, diols, hydrocarbon, mineral oil, mineral oil derived products, halogenated compounds and aromatic compounds.

20. The method of claim 1 wherein said conditions suitable for selection comprise culturing said microorganism in the presence of elevated temperature.

21. The method of claim 20 wherein said elevated temperature is about 42° C. to about 48° C.

22. The method of claim 1 wherein said conditions suitable for selection comprise culturing said microorganism in the presence of high salt.

23. The method of claim 1 wherein said microorganism is selected from the group consisting of Gram-positive or a Gram-negative microorganism, fungus, yeast or eukaryotic cells.

24. The method of claim 23 wherein said microorganism is an Enterobacteriaceae.

25. The method of claim 24 wherein said microorganism is an Escherichia.

26. The method of Claim wherein said microorganism is E.coli.

27. The method of claim 25 wherein said microorganism is E. blattae.

28. The method of claim 1 wherein said evolved microorganism is E.coli having ATCC accession number PTA-91.

29. The method of claim 1 wherein said evolved microorganism is E.blattae having ATCC accession number PTA-92.

30. An expression vector comprising a mutator gene and a temperature sensitive origin of replication.

31. The expression vector of claim 30 wherein said mutator gene is a mutated MutD.

32. The expression vector of claim 31 wherein said mutated MutD has at least one nucleotide mutation in the naturally occurring MutD sequence (SEQ ID No. 1) selected from the group consisting of C44T, T218G, T369C, C418T, T451C, G484A, C491T, A661C, A665C, T673A, C688T, A706G, T715C and A727G.

33. A host cell comprising the expression vector of claim 30.

34. The host cell of claim 33 that is a Gram-positive or Gram-negative microorganism.

35. The host cell of claim 34 that is an Enterobacteriaceae.

36. The isolated E. blattae microorganism deposited with the ATCC and having accession number PTA-92.

37. The isolated E.coli microorganism deposited with the ATCC and having accession number PTA-91.

38. A method for preparing an evolved microorganism comprising the steps of:
   a. mutating a DNA repair gene in a microorganism to obtain a mutated strain,
   b. culturing the mutated strain for at least 20 doublings under conditions suitable for selection of an evolved strain, wherein said mutated strain generates a mutation rate of at least 5–100,000 fold relative to the wild-type microorganism, and
   c. restoring the naturally occurring DNA repair gene in said evolved microorganism.

* * * * *